United States Patent [19]
Hausheer et al.

[11] Patent Number: 5,955,467
[45] Date of Patent: Sep. 21, 1999

[54] PHARMACEUTICAL FORMULATIONS OF POORLY WATER SOLUBLE CAMPTOTHECIN ANALOGUES AND NMP

[75] Inventors: Frederick H. Hausheer; Kochat Haridas; Dhanabalan Murali; Dasharatha Gauravaram Reddy, all of San Antonio, Tex.

[73] Assignee: BioNumerik Pharmaceuticals, Inc., San Antonio, Tex.

[21] Appl. No.: 08/955,956

[22] Filed: Oct. 22, 1997

Related U.S. Application Data

[62] Division of application No. 08/461,385, Jun. 5, 1995, Pat. No. 5,726,181.

[51] Int. Cl.$^6$ .................................................. A61K 31/44
[52] U.S. Cl. ......................................... 514/283; 514/423
[58] Field of Search ...................................... 514/283, 423

[56] References Cited

U.S. PATENT DOCUMENTS

| | | |
|---|---|---|
| 4,473,692 | 9/1984 | Miyasaka et al. . |
| 4,545,880 | 10/1985 | Miyasaka et al. . |
| 4,772,589 | 9/1988 | Kaplan et al. . |
| 4,778,891 | 10/1988 | Tagawa et al. . |
| 5,034,397 | 7/1991 | Kaplan et al. . |
| 5,061,800 | 10/1991 | Yaegashi et al. . |

FOREIGN PATENT DOCUMENTS

90/14094  11/1990  WIPO .

OTHER PUBLICATIONS

Moertel et al. Cancer Chemotherapy Reports 56:95, 1972.

Barilero, et al., Simultaneous determination of the camptothecin analogue CPT–11 and its active metabolite SN –38 by high–performance liquid chromatography: application to plasma pharmacokinetic studies in cancer patients, Journal of Chromatography, 575 (1992) 275–280.

Bates, T. et al., Solubilizing Properties of Bile Salt Solutions I. Effect of Temperature and Bile Salt Concentration on Solubilization of Glutethimide, Griseofulvin, and Hexestrol. Journal of Pharmaceutical Sciences 55:191–199, (1966).

Bates, T. et al., Rate of Dissolution of Griseofulvin and Hexestrol in Bile Salt Solutions, Chemical Abstracts, 65:8680b, 1966.

Bates, T. et al., Solubilizing Properties of Bile Salt Solutions II. Effect of inorganic electrolyte, lipids and a mixed bile salt system on solubilization of glutethimide, griseofulvin, and hexestrol., Chem. Abstracts 64 : 9517e 1966; Journal of Pharm. Sci. 55(9), 901–6 (1966)(Eng.).

Clavel, M. et al., Phase I Study of the Camptothecin Analogue CPT–11 administered as a daily infusion for 3 consecutive days; Proceedings of the American Association for Cancer Research 33:262 1568 (1992).

Creaven, P.J. et al., Plasma Camptothecin (NSC–100880) Levels During a 5–Day Course of Treatment: Relation to Dose and Toxicity; Cancer Chemotherapy Reports Part 1 56:573–578 (1972).

Culine S. et al., Phase I Study of the Camptothecin Analog CPT–11, Using a Weekly Schedule (Meeting Abstract) Proc. of Amer. Soc. Clin. Onc.; 11:110 (1992).

Emerson, D.L., In Vivo Antitumor Activity of Two New Seven–substituted Water–soluble Camptothecin Analogues; Cancer Research; 55:603–609 (1995).

Fukuoka M. et al., A Phase II Study of CPT–11, a New Derivative of Camptothecin, for Previously Untreated Non–Small–Cell Lung Cancer; Journal of Clinical Oncology, 10(1):16–20, (1992).

Giovanella, B. et al., DNA Topoisomerase I–Targeted Chemotherapy of Human Colon Cancer in Xenografts; Science 246:1046–1048 (1989).

Gottlieb, J. et al., Preliminary Pharmacologic and Clinical Evaluation of Camptothecin Sodium (NSC–100880); Cancer Chemotherapy Reports Part 1 54:461–470, (1970).

Gottlieb, J. et al., Treatment of Malignant Melanoma With Camptothecin (NSC–100880); Cancer Chemotherapy Reports Part 1 56:103–105, (1972).

Hsiang, et al., Arrest of Replication Forks by Drug–stabilized Topoisomerase I–DNA Cleavable Complexes as a Mechanism of Cell Killing by Camptothecin; Cancer Research 49:5077–5082, (1989).

Houghton, P. et al., Therapeutic Efficacy of the Topoisomerase I inhibitor 7–Ethyl–10–(4–[1–piperidino]–1–piperidino)—carbonyloxy–camptothecin against Human Tumor Xenografts: Lack of Cross–Resistance in Vivo in Tumors with Acquired Resisance to the Topoisomerase I Inhibitor 9–Dimethylaminomethyl–10–hydroxycamptothecin; Cancer Reasearch 53:2823–2829, (1993).

Jaxel, C. et al., Structure–Activity Study of the Actions of Camptothecin Derivatives on Mammalian Topoisomerase I: Evidence for a Specific Receptor Site and a Relation to Antitumor Activity; Cancer Research 49:1465–1469, (1989).

(List continued on next page.)

*Primary Examiner*—Rebecca Cook
*Attorney, Agent, or Firm*—Thomas J. Dodd

[57] ABSTRACT

A- and/or B-ring substituted camptothecin derivatives, which are poorly water soluble (less than 5 micrograms per milliliter of water), are highly lipophilic camptothecin derivatives (HLCD) and are very active against a variety of human cancers. Because of their very poor water solubility, HLCD have not been used to treat human patients with cancer due to the inability to administer sufficient quantities of the HLCD dissolved in a pharmaceutical formulation. This invention overcomes these limitations by teaching novel pharmaceutically acceptable HLCD formulations for the direct administration of HLCD to human patients with cancer. The claimed invention also describes the methods to create solutions of HLCD and antitumor compositions of HLCD to allow the administration of HLCD in sufficient amounts to treat human patients with various types of cancer. This invention is also directed to injectable sterile solutions, antitumor compositions, solutions and suspensions comprising N-methyl-2-pyrrolidinone and a highly lipophilic camptothecin derivative.

25 Claims, No Drawings

OTHER PUBLICATIONS

Kaneda, N. et al., Metabolism and Pharmacokinetics of the Camptothecin Analogue CPT–11 in the Mouse; Cancer Research 50:1715–1720, (1990).

Kano, Y. et al., Effects of CPT–11 in Combination with Other Anti–Cancer Agents in Culture; Int. J. Cancer, 50:604–610 (1992).

Kanzawa, F. et al., Role of Carboxylesterase on Metabolism of Campthothecin Analog (CPT–11) in Non–Small Cell Lung Cancer Cell Line PC–7 Cells; Proceedings of the American Association for Cancer Research, 33:A2552, (1992).

Kawato, Y. et al., Intracellular Roles of SN–38, a Metabolite of the Camptothecin Derivative CPT–11, in the Antitumor Effect of CPT–11; Cancer Research 51:4187–4191, (1991).

Kunimoto, T. et al., Antitumor Activity of 7–Ethyl–10–[4–(1–piperidino)–1–piperidino] carbonyloxy–camptothecin, against Murine Tumors; Cancer Research 47:5944–5947, (1987).

Luzzio, M.J. et al., Synthesis and Antitumor Activity of Novel Water Soluble Derivatives of Camptothecin as Specific Inhibitors of Topoisomerase I. J. Med. Chem. 38:395–401, (1995).

Malone, M. et al.,, Desoxycholic Acid Enhancement of Orally Administered Reserpine; Journal of Pharmaceutical Sciences, 55:972–974, (1966).

Masuda, N. et al., CPT–11: A New Derivative of Camptothecin for the Treatment of Refractory or Relapsed Small–Cell Lung Cancer; Journal of Clinical Oncology, 10(8):1225–1229, (1992).

Moertel, C., et al., Phase II Study of Camptothecin (NSC–100880) in the Treatment of Advanced Gastrointestinal Cancer; Cancer Chemotherapy Reports Part I, 56(1):95–101 (1972).

Muggia, F., et al., Phase I Clinical Trial of Weekly and Daily Treatment With Camptothecin (NSC–100880): Correlation With Preclinical Studies; Cancer Chemotherapy Reports Part 1, 56(4):515–521, (1972).

Negoro, S., et al., Phase I Study of Weekly Intravenous Infusions of CPT–11, a New Derivative of Camptothecin in the Treatment of Advanced Non–Small–Cell Lung Cancer; Journal of the National Cancer Institute, 83(16): 1164–1168, (1991).

Negoro, S., et al., Phase II Study of CPT–11, New Camptothecin Derivative, In Small Cell Lung Cancer (SCLC) (Meeting Abstract); Proc. Annu. Meet. Am. Soc. Clin. Oncol. 10:A822, (1991).

Niimi, S., et al., Mechanism of Cross–Resistance to a Camptothecin Analogue (CPT–11) in a Human Ovarian Cancer Cell Line Selected by Cisplatin; Cancer Research 52:328–333, (1992).

Ohe, Y., et al., Phase I Study and Pharmacokinetics of CPT–11 With a 5–Day Continuous Infusion; Journal of the National Cancer Institute; 84(12):972–974, (1992).

Ohno, R., et al., An Early Phase II Study of CPT–11: A New Derivative of Camptothecin, for the Treatment of Leukemia and Lymphoma; Journal of Clinical Oncology; 8(11):1907–1912, (1990).

Pantazis, P., et al., Cytotoxic Efficacy of 9–Nitrocamptothecin in the Treatment of Human Malignant Melanoma Cells in Vitro; Cancer Research; 54:771–776, (1994).

Pommier, Y., et al., Camptothecins: Mechanisms of Action and Resistance; Cancer Investigation, Presented at the "Chemotherapy Foundation Symposium X Innovative Cancer Chemotherapy for Tomorrow," p. 3, 1992.

Potmesil, M., et al., Preclinical and Clinical Development of DNA Topoisomerase I Inhibitors in the United States. in Andoh, T., Ikeda, H. Oguro, M. (eds) : Molecular Biology of DNA Topoisomerases and Its Application to Chemotherapy. Boca Raton, FL., CRC Press, Inc. 301–311, (1993).

Rivory, L.P., et al., Kinetics of the Vivo Interconversion of the Carboxylate and Lactone Forms of Irinotecan (CPT–11) and of Its Metabolite SN–38 in Patients; Cancer Research; 54:6330–6333, (1994).

Rothenberg, M.L., et al., A Phase I and Pharmacokinetic Trial of CPT–11 in Patients With Refractory Solid Tumors (Meeting Abstract); Amer. Soc. Clin. Onc.; 11:113, (1992).

Rothenberg, M.L., et al., Phase I and Parmacokinetic Trial of Weekly CPT–11; 11:2194–2204, (1993).

Rowinsky, E. et al., Phase I and Pharmacologic Study of CPT–11, A Semisynthetic Topoisomerase I–Targeting Agent, On a Single–Dose Schedule (Meeting Abstract); Proc. of Amer. Soc. Clin. Onc.; 11:115, (1992).

Sawada, S. et al., Synthesis and Antitumor Activity of 20(s)–Camptothecin Derivatives: Carbamate–Linked, Water Derivatives of 7–Ethyl–10–hydroxycamptothecin; Chem. Pharm. Bull.; 39(6):1446–1454, (1991).

Shimada, Y. et al., Phase II Study of CPT–11, New Camptothecin Derivative, In the Patients with Metastatic Colorectal Cancer; Proc. of Amer. Soc. Clin. Onc., 10:135, (1991).

Supko, J. et al., Pharmacokinetics of the 9–Amino and 10, 11–Methylenedioxy Derivative of Camptothecin in Mice; Cancer Research; 53:3062–3069, (1993).

Takeuchi, S. et al., Late Phase II Study of CPT–11, A Topoisomerase I Inhibitor, In Advanced Cervical Carcinoma (CC) (Meeting Abstract); Proc. of Amer. Soc. Clin. Onc.; 11:224, (1992).

Wall, M.E. et al., Camptothecin and Taxol: Discovery to Clinic–Thirteenth Bruce F. Cain Memorial Award Lecture; Cancer Research; 55:753–760, (1995).

Wall, M.E. et al., Camptothecin, in Cassady JM, Douros JD (eds): Anticancer Agents Based on Natural Product Models, San Diego, California; Academic Press 417–436, (1980).

Wall, M.E. et al., Plant Antitumor Agents: Synthesis and Structure Activity of Novel Camptothecin Anaglogs; J. Med. Chem.; 36:2689–2700, (1993).

Westergaard, H. et al., The Mechanism Whereby Bile Acid Micelles Increase the Rate of Fatty Acid and Cholesterol Uptake into the Intestinal Mucosal Cell; The Journal of Clinical Investigation; 58:97–108, (1976).

PHARMACEUTICAL FORMULATIONS OF POORLY WATER SOLUBLE CAMPTOTHECIN ANALOGUES AND NMP

This Application is a division of application Ser. No. 08/461,385, filed Jun. 5, 1995, now U.S. Pat. No. 5,726,181.

BACKGROUND OF THE INVENTION

1. Field of the Invention

During the past three decades it has been observed that camptothecin (CPT) and most of the highly lipophilic derivatives of camptothecin (HLCD) in their lactone form are poorly water soluble. For example, less than 5 micrograms of drug will dissolve in one milliliter of water to form a solution at a pH of 2 to 6. A range of pH from 2 to 6 maintains the dissolved camptothecin in the lactone form. Camptothecin and many of its poorly water soluble derivatives are known potent anticancer drugs, however, their very poor water solubility has prevented their use in the treatment of human cancer. The potency of these anticancer drugs was determined by their ability to inhibit in vitro and in vivo tumor cell growth. This invention solves the poor solubility problems of camptothecins and its derivatives. Thus, the purpose of this invention is to overcome the poor solubility of highly lipophilic camptothecin derivatives in their lactone form by designing novel formulations of the drug (at sufficient concentrations) which can be administered orally, topically or parenterally for the purpose of treating human patients with cancer.

2. Description of the Related Art

Introduction

A. DNA Topoisomerases

Several clinically important anticancer drugs kill tumor cells by affecting DNA topoisomerases. Topoisomerases are essential nuclear enzymes that function in DNA replication and tertiary structural modifications, such as overwinding, underwinding, and catenation, which normally arise during cellular replication, transcription, and perhaps other DNA processes. Two major topoisomerases have been identified, both of which are ubiquitous to eukaryotic cells: (1) Topoisomerase I (topo I) cleaves single stranded DNA; and (2) Topoisomerase II (topo II) cleaves double stranded DNA. Topoisomerase I is involved in DNA replication; it relieves the torsional strain introduced ahead of the moving replication fork.

Topoisomerase I, purified from human colon carcinoma cells or calf thymus, has been shown to be inhibited by camptothecin and many of its derivatives. Camptothecin, and water soluble camptothecin derivatives including CPT-11, topotecan, 9-amino camptothecin, 9-nitro camptothecin, DX8951 and 7-(4-methylpiperazinomethylene)-10,11-methylenedioxy camptothecin, 10,11-methylenedioxy camptothecin and 10,11-ethylenedioxy camptothecin have either been studied preclinically or used in clinical trials to treat certain types of human cancer. To date, there have been no clinical studies in human patients involving poorly water soluble highly lipophilic camptothecins, other than for camptothecin (in the late 1970's).

This absence of clinical use of lipophilic camptothecins has been due to the lack of pharmaceutical formulations which allow the direct administration of the poorly water soluble camptothecin lactone species to human patients with cancer. For the purpose of this invention, examples of highly lipophilic camptothecin derivatives include camptothecin, 10-hydroxy-7-ethyl camptothecin (SN38), 7-ethyl camptothecin (SN22), 10,11-methylenedioxy camptothecin, 10,11-ethylenedioxy camptothecin and other poorly water soluble derivatives of camptothecin which are active antitumor agents.

For the purpose of this invention, poorly water soluble and highly lipophilic camptothecin derivatives (referred to as "HLCD" for the purposes of this invention) are defined interchangeably as any A- and/or B-ring substituted camptothecin which have a water solubility of less than 5 micrograms per milliliter of water. Also for the purposes of the instant invention, the terms "highly lipophilic" and "poorly water soluble" are used interchangeably to describe their fundamental bioavailability and chemical behavior. Poorly water soluble camptothecin derivatives use the same mechanism to inhibit Topo I; they stabilize the covalent complex of enzyme and strand-cleaved DNA, which is an intermediate in the catalytic mechanism. These compounds have no binding affinity for topoisomerase I but do bind with measurable affinity to the enzyme-DNA complex. The stabilization of the topoisomerase I "cleavable complex" by camptothecin and its derivatives is readily reversible.

Although camptothecin and the aforementioned poorly water soluble camptothecin derivatives have no effect on topoisomerase II, these camptothecin derivatives stabilize the Topoisomerase I-DNA "cleavable complex" in a manner analogous to the way in which epipodophyllotoxin glycosides and various anthracyclines inhibit topoisomerase II.

Inhibition of topoisomerase I by camptothecin and highly lipophilic camptothecin derivatives induces protein-associated DNA single-strand breaks. Virtually all of the DNA strand breaks observed in vitro cells treated with camptothecin are protein linked. However, an increase in unexplained protein-free breaks can be detected in L1210 cells treated with camptothecin. The compounds appear to produce identical DNA cleavage patterns in end-labeled linear DNA. It has not been demonstrated that camptothecin or highly lipophilic camptothecin derivatives cleaves DNA in the absence of the topoisomerase I enzyme.

B. Activity of Highly Lipophilic Camptothecin Derivatives is Cell Cycle Specific The activity of highly lipophilic camptothecin derivatives is cell cycle specific. The greatest quantitative biochemical effect observed in cells exposed to camptothecin and its derivatives is DNA single-strand breaks that occur during the S-phase. Because the S-phase is a relatively short phase of the cell cycle, longer or repetitive exposures to the drugs results in increased cell killing. Brief exposure of tumor cells to the drugs produces little or no cell killing, and quiescent cells are refractory. These results are likely due to two factors:

(1) The drugs inhibit topoisomerase I reversibly. Although they may produce potentially lethal modifications of the DNA structure during DNA replication, the breaks may be repaired after washout of the drug; and (2) Cells treated with topo I inhibitors, such as camptothecins tend to stay in G0 of the cell cycle until the drug is removed and the cleaved DNA is repaired. Inhibitors of these enzymes can affect many aspects of cell metabolism including replication, transcription, recombination, and chromosomal segregation.

C. Lactone Form of Highly Lipophilic Camptothecin Derivatives Increases Antitumor Activity and Reduces Water Solubility Utilizing HPLC and NMR techniques, researchers have demonstrated that camptothecin and many of it's derivatives undergo an alkaline, pH-dependent hydrolysis of the E-ring lactone. The slow reaction kinetics allows one to assess whether both the lactone and non-lactone forms of the drug stabilizes the topoisomerase I-cleaved DNA complex. Studies indicate that only the closed lactone form of the drug helps stabilize the cleavable complex. This observation provides reasoning for the high degree of drug activity observed in solid tumor models. Tumor cells, particularly hypoxic cells prevalent in solid neoplasms, have relatively lower intracellular pH levels than normal cells. At pH levels below 7.0, the lactone E-ring form of camptothecins predominates. Thus, the inventors believe that camptothecins will be more effective at inhibiting topoisomerase I in an acidic environment than in cells having higher intracellular pH levels.

One of the objects of this invention is to provide lactone stable poorly water soluble camptothecin derivatives as the basis of the claimed subject matter. For this invention, lactone stable camptothecin derivatives are defined as poorly water soluble A- and/or B-ring substituted camptothecins which are dissolved in N-methyl-2-pyrrolidinone (referred to as "NMP") in the presence of an acid with or without additional excipients as desired. The inventors have discovered that highly lipophilic camptothecins display an unusually high degree of solubility (greater than 1.0 mg per milliliter) in N-methyl-2-pyrrolidinone (referred to as "NMP"). NMP, as a pharmaceutical excipient, is safe for human administration and has been found by the inventors to be chemically inert with respect to poorly water soluble camptothecins. The presence of an acid in the solution further stabilizes the lactone E-ring form of the HLCD; this is particularly useful when additional excipients are used and when the drug formulation is diluted with aqueous media. For the purpose of this invention, lactone stable camptothecin and highly lipophilic camptothecin are used interchangeably.

D. Camptothecin and Highly Lipophilic Camptothecins

In 1966, Wall and Wani isolated camptothecin from the plant, *Camptotheca acuminata*. In the early 1970's camptothecin reached Phase I and Phase II human trials and was found to have antitumor activity, but it caused unpredictable myelosuppression and hemorrhagic cystitis. It is important to note that all of these studies used sodium hydroxide formulations of camptothecin which greatly increased the water solubility of the molecule due to base mediated hydrolysis of the lactone E-ring to form the carboxylate species of camptothecin in appreciable quantities. At that time, however, it was not recognized that the lactone E-ring species of camptothecin had significantly (e.g., greater than 10 fold) greater antitumor activity than the carboxylate form of camptothecin. Phase II studies with sodium camptothecin were limited because patients given sodium camptothecin experienced unpredictable and severe myelosuppression, gastrointestinal toxicity, hemorrhagic cystitis, and alopecia. Clinical trials with sodium camptothecin (referred to as "SCPT" for the purposes of this invention) were eventually discontinued because of these unpredictable toxicities and the lack of consistent antitumor activity.

To demonstrate the utility and novelty of the present invention, it is useful to review the literature on human clinical trials conducted with SCPT administered parenterally to human patients with cancer. Gottlieb and coworkers (Cancer Chemotherapy Reports 54:461; 1970) reported on clinical studies with the sodium salt of camptothecin (SCPT) which were begun at the Baltimore Cancer Research Center in January 1969. In this clinical trial, SCPT was administered as a rapidly running i.v. solution over a 5–10 minute period at a concentration of 2 mg of SCPT per milliliter of saline. Doses of SCPT ranged from 0.5 to 10.0 mg/kg of actual or ideal body weight (whichever was less). These investigators reported that because hemorrhagic cystitis was noted in several of the early trials, patients receiving camptothecin sodium were well hydrated either i.v. or orally for 72 hours after drug administration. It is interesting to note that the mean urine recovery of camptothecin was 17.4% over the first 48 hours (range: 3.6–38.9%) with most of the drug excretion occurring in the initial 12 hours. When these investigators excluded the 5 patients with impaired urinary excretion, the mean urine recovery of camptothecin was 22.8%. These investigators noted that unmetabolized camptothecin in high concentrations rapidly appeared in the urine after i.v. drug administration and went further to state that this finding probably accounted for the sterile hemorrhagic cystitis noted in 3 moderately dehydrated patients. Although maintaining a copious urine outflow seemed to prevent this complication, the investigators explored various alterations in urine pH as another possible way of decreasing the risk of this debilitating type of toxicity.

Muggia et. al. (Cancer Chemotherapy Reports 56:515; 1972) reported results of a Phase I clinical trial in fifteen patients treated with SCPT at four weekly dose levels ranging from 20–67 mg/m$^2$. No clinical benefit was observed in eight patients with measurable disease who were treated with the 5-day courses at dose levels associated with toxicity. The drug was administered in concentrations of 1 to 10 mg/ml and it was always administered by intravenous push. Cystitis was the most prominent non-hematologic toxic effect observed in this study. Bladder toxicity was dose limiting in three patients receiving doses of 20 to 30 mg/m$^2$, and occurred in two additional patients at doses of 44 and 30 mg/m$^2$. Cystitis, another toxic effect occurring frequently after treatment with SCPT, was not predicted by preclinical toxicologic studies. Their clinical experience suggested that the occurrence of cystitis may be related to the duration of the patient's exposure to the drug when administered as the carboxylate form. Camptothecin is excreted unchanged by the kidneys, although a large percentage of the drug administered cannot be accounted for in the urine and is likely conjugated in the liver to form the glucuronide and excreted via the hepatobiliary route. It is possible that relatively less drug is excreted in the urine of animals since an extremely active transport of camptothecin into bile has been demonstrated. Alternatively, these investigators postulated that the mucosa of the human bladder is more susceptible to the toxic action of camptothecin or that the effect on the human bladder is due to some unrecognized camptothecin metabolite.

Moertel and coworkers reported results of a Phase II Study of Camptothecin (NSC-100880) in the Treatment of Advanced Gastrointestinal Cancer (Cancer Chemotherapy Reports 56:95; 1972.) These investigators administered camptothecin sodium dissolved in physiologic saline at a concentration of 2 mg/ml and administered by rapid intravenous infusion over 5–10 minutes. Two schedules of administration were used in this study: (a) a single injection repeated at 3-week intervals; and (b) a 5-day course repeated ever 4 weeks. The initial dose for the single-dose method was 180 mg/m$^2$. Because of toxic effects which were considered excessive by the investigators, later patients were treated at doses ranging between 90 and 120 mg/m$^2$. Dosages for the 5-day course ranged between 11 and 22 mg/m$^2$/day (total course, 55–110 mg/m$^2$). Diarrhea was only a problem at higher doses, but then could be quite severe to the point of fecal incontinence and persistent for as long as 4 weeks. Cystitis usually began about 7–10 days after treatment and was characterized clinically by dysuria and frequency. With more severe toxicity, gross hematuria developed. Pathologically, this was characterized by multiple necrotic ulcerations which could involve the entire urinary tract from kidney pelvis to bladder. According to these investigators, the occurrence of hemorrhagic cystitis did not preclude further treatment with camptothecin, and its severity could be titrated down by lowering the dose in subsequent courses. These investigators also reported that the more prolonged schedule produced more severe toxicity at a given total dose level, but the difference was not as great as might have been predicted by preclinical animal studies. These investigators proposed that a reasonable initial dose of SCPT is 110–120 mg/m$^2$ for the single-injection method or 17 mg/m$^2$/day (total dose, 85 mg/m$^2$) for the 5-day course. They noted that after 2 months (8 or 9 weeks) only two of their 61 patients showed evidence of partial objective improvement, and none showed improvement at 3 months. Both patients who demonstrated an objective response at 2 months had large bowel cancer. These investigators concluded that camptothecin "is a drug of protean and unpredictable toxicity that has no clinical value in the management of gastrointestinal cancer." See Tables 1, 2, 3, and 4.

TABLE 1

Toxic Reactions: Single-Dose Administration of
Sodium Camptothecin (Moertel et. al. Cancer Chemotherapy
Reports 56:95; 1972.)
Nonhematologic Toxicity No. of patients with:

| Dose (mg/m$^2$) | No. of patients treated | Diarrhea | Cystitis |
|---|---|---|---|
| 90 | 10 | — | 1 |
| 100 | 6 | — | 2 |
| 110 | 2 | 1 | 1 |
| 120 | 7 | 4 | 2 |
| 180 | 9 | 2 | 3 |

TABLE 2

Toxic Reactions: 5 Consecutive Day Administration
of Sodium Camptothecin (Moertel et. al. Cancer Chemotherapy
Reports 56:95; 1972.)
Nonhematologic No. of patients with:

| Dose (mg/m$^2$ × 5) | No. of patients treated | Diarrhea | Cystitis |
|---|---|---|---|
| 11 | 2 | — | 1 |
| 15 | 9 | 1 | 4 |
| 17 | 5 | 4 | 2 |
| 20 | 10 | 4 | 6 |
| 22 | 1 | 1 | — |

TABLE 3

Relationship of Method of Administration to Cystitis
(Moertel et. al. Cancer Chemotherapy Reports 56:95; 1972.)
Method of administration

| | Single dose | 5-Day course |
|---|---|---|
| Cystitis | (% of 34 patients) 24 | (% of 27 patients) 48 (P < 0.05) |

TABLE 4

Objective Responses (Moertel et. al. Cancer
Chemotherapy Reports 56:95; 1972.)

Single-dose method (34 patients)

| | Time after start of therapy | | | |
|---|---|---|---|---|
| Objective Responses* | 3 wks | 6 wks | 9 wks | 12 wks |
| Improved | 4 | 2 | 2 | — |
| Stable | 17 | 11 | 8 | 6 |
| Worse | 13 | 21 | 24 | 28 |

5-Day course (27 patients)

| | Time after start of therapy | | |
|---|---|---|---|
| Objective Responses* | 4 wks | 8 wks | 12 wks |
| Improved | 1 | — | — |
| Stable | 12 | 7 | 6 |
| Worse | 14 | 20 | 21 |

*3 patients showed 25%–50% response at 3 wks only

Gottlieb and Luce reported the results of treatment of patients with malignant melanoma with camptothecin sodium (Cancer Chemotherapy Reports 56:103, 1972). Fifteen patients with advanced malignant melanoma were treated with SCPT at doses of 90–360 mg/m$^2$ repeated every 2 weeks. SCPT was administered as a single rapid intravenous (i.v.) injection starting at a dose of 120 mg/m$^2$ repeated at 2-week intervals. The dose in subsequent courses was increased by increments of 60 mg/m$^2$ per dose (to a maximum of 360 mg/m$^2$) in eight patients who tolerated their initial doses with minimal toxicity. To prevent the known bladder toxicity of this drug, patients were well hydrated for 3 days after therapy. None of the patients had a 50% or greater decrease in tumor diameter. Less pronounced transient tumor regression was noted in three patients, but no clinical benefit was associated with these responses. The remaining patients had no change or progressions in their disease. Toxic effects included myelosuppression (11 patients), nausea and vomiting (9 patients), alopecia (8 patients), diarrhea (3 patients), and hemorrhagic cystitis (1 patient). These investigators concluded that SCPT, at least as administered in this study, had little to offer the patient with advanced disseminated melanoma.

Creaven and co-investigators reported studies of plasma camptothecin levels during a 5 consecutive day course of treatment (Cancer Chemotherapy Reports 56:573–578, 1972). These investigators state that the toxicity of SCPT has been widely and unpredictably variable in the course of initial clinical evaluation. Severe toxic effects including cystitis occurred even though patients with obvious renal disease were excluded. In this study they investigated plasma camptothecin levels 24 hours after the administration of SCPT administered on a once daily×5 schedule to determine whether such measurements would be of value in predicting toxicity, and observed that plasma camptothecin levels have little relation to the dose given when the dose is in the range of 6.5–20 mg/m$^2$/day.

In another clinical study Muggia and co-workers reported the results of a Phase I Trial of weekly and daily treatment with SCPT (Cancer Chemotherapy Reports 56: 515–521, 1972). Fifteen patients were treated at four weekly dose levels ranging from 20 to 67 mg/m$^2$ of SCPT. Reversible leukopenia was the major dose-limiting toxic effect. Five-day loading courses were begun at total doses of 1.5 mg/mr$^2$ per course because increased sensitivity to daily administration had been noted in animal studies. Leukopenia was more prolonged after daily treatment than after weekly treatment and occurred in four of six patients receiving a total dose of 100 mg/m². Tolerance to 5-day courses was an unexpected clinical result. Also unpredicted by preclinical studies was human susceptibility to cystitis with either schedule of treatment. They noted clinical responses in two of ten patients in whom responses could be evaluated after weekly courses of treatment. No clinical benefit was observed in eight patients with measurable disease who were treated with the 5-day courses at dose levels associated with toxicity. Cystitis was another toxic effect occurring frequently after treatment with SCPT, and this toxicity was lo not predicted by preclinical toxicologic studies. The investigators suggested that the occurrence of cystitis may be related to the duration of the patient's exposure to the drug, and proposed that camptothecin is excreted unchanged by the kidneys, although a large percentage of the drug administered cannot be accounted for in the urine. They also proposed from this study that it is possible that relatively less drug is excreted in the urine of animals since an extremely active transport of camptothecin into bile had been demonstrated. They also postulated that the mucosa of the human bladder is more susceptible to the toxic action of camptothecin or that the effect on the human bladder is due to some unrecognized camptothecin metabolite.

There are several features which are common in these earlier clinical studies with SCPT. First is the use of SCPT ("SCPT") which made the camptothecin more water soluble. Hydrolysis of the lactone E-ring to form the water soluble carboxylate species was accomplished by formulating camptothecin in sodium hydroxide. The antitumor activity of the carboxylate form of camptothecin is reduced by at least 10-fold, which partially accounts for the lack of clinical response in these studies. Second is the rapid intravenous administration of the drug. Camptothecin is an S-phase specific drug and therefore will exert a greater antitumor effect under conditions of prolonged or repetitive exposure, as in a continuous intravenous infusion or repetitive daily dosing. The short infusion (i.v. push or rapid i.v. infusion) times in all of these earlier studies do not allow a long enough exposure time to the drug to attain suitable plasma drug levels, and is further compounded by the administration of the water soluble carboxylate form of camptothecin. A third common feature is the notable frequency of cystitis in these studies using water soluble SCPT.

The novel features of the present invention includes the following: (1) pharmaceutically acceptable formulations which allow direct parenteral administration of lactone stable highly lipophilic camptothecin derivatives to human patients with cancer (referred to as "HLCD"); (2) pharmaceutically acceptable formulations which allow the direct oral administration of lactone stable HLCD to human patients with cancer. The inventors predict that by administering the carboxylate species of HLCD a higher incidence of renal toxicity is likely to be observed than if the lactone species of HLCD is administered to patients.

The inventors maintain that the previous use of SCPT caused hemorrhagic cystitis relates to the enhanced renal excretion of the carboxylate form of camptothecin which when exposed to the lower pH (~pH 6 or less) of the distal convoluted tubule and collecting duct in the kidney, as significant proportions of the carboxylate form of camptothecin is converted into the lactone form. The formation of the lactone species in high concentration at the distal convoluted tubule and collecting duct resulted in a high concentration of the lactone form of camptothecin being excreted and damaging the uroepithelium which resulted in hemorrhagic cystitis. Elimination of a greater concentration of the lactone form of camptothecin by the renal route is enhanced by administration of the water soluble carboxylate form and is greatly reduced by administration of the lactone form of the drug. Thus, additional significant utilities of the present invention are that the administration of HLCD substantially in the lactone form orally or parenterally to cancer patients will significantly reduce the renal elimination of HLCD and further that the incidence of hemorrhagic cystitis will be significantly reduced in patients who receive the formulations of HLCD claimed in this invention.

In addition to the previously noted toxicities and limited clinical responses to camptothecin, HLCD have also been considered unsuitable for clinical use because they are all poorly soluble in water (e.g. less than 5 micrograms of HLCD per milliliter of water). The poor water solubility of HLCD requires the use of large volumes of water-based parenteral vehicle, which results in administering the drug for a prolonged period of time and causes inconvenience and discomfort to patients. Also, administering the drug for prolonged period of time increases the costs associated with treatment of patients. Hence, an HLCD formulation which permits higher concentrations of the active drug in the infusion after dilution with a suitable parenteral vehicle is desired. Also desired is that the drug remains in the diluted solution for sufficient amount of time to be effective. Such an infusion solution will be greatly beneficial to patients, by bringing down the time required for administering useful amounts of drug and also the costs associated with administering the drug for a more prolonged period of time.

One highly useful purpose of this invention is to formulate the HLCD in a pharmaceutically acceptable manner using an organic or a mixture of organic co-solvents with a high degree of physiologic safety to dissolve the HLCD in desirable concentrations and concurrently stabilize HLCD in the lactone E-ring form. It is this formulation invention which permits direct administration of HLCD to human patients with cancer.

The inventors believe that direct administration of a lactone stable HLCD to human patients has another important utility for treating patients with cancer. It is well known that cell membranes are comprised largely of lipid, and that lipid soluble drugs in general have superior ability to penetrate hydrophobic cellular membranes relative to water soluble drugs. HLCD are poorly water soluble and are therefore lipid soluble which facilitates their penetration into various body tissues and will improve the bioavailability and anticancer activity of the drug. The anticancer activity of the camptothecins in general is closely linked with their ability to inhibit the intracellular Topoisomerase I which is concentrated within the nucleus of the cell. The inventors contend that the present invention increases the amount of HLCD drug diffusion through the cellular and nuclear membranes in tumor cells and will result in superior antitumor activity of the drug. Water soluble camptothecin derivatives are predicted to have a lesser ability to diffuse through the cellular and nuclear membranes in the body.

The utility of suitable organic solvents for this invention involving pharmaceutical dosage forms of HLCD is restricted to those which have a high degree of physiological safety in humans. This invention teaches new methods for making pharmaceutical formulations for a variety of lactone stable HLCD with water solubility of 5 micrograms per milliliter or less. Some examples of poorly water soluble camptothecins (HLCD) include 10,11-methylenedioxy camptothecin, 10,11-ethylenedioxy camptothecin, 7-ethyl camptothecin(SN22), 7-ethyl-10-hydroxy camptothecin (SN38) and congeners thereof. Any poorly water soluble camptothecin with a solubility of 5 micrograms per milliliter of water or less may be dissolved or suspended in these novel formulations and will have appreciable quantities (greater than 90%) of the lactone form of drug in the resulting solution. 10,11-Methylenedioxy camptothecin, 10,11-ethylenedioxy-camptothecin, 7-ethyl camptothecin, and 7-ethyl-10-hydroxy camptothecin and congeners thereof are reportedly very active in preclinical studies, but they are also reported to be poorly soluble in water (less than 5 micrograms of drug will dissolve in one milliliter of water) which limits their utility because of the inability to readily administer these drugs to human patients with cancer (Pommier, et al. 1992, Wall et. al. 1994).

One of the advantages of the instant invention is that the instant formulations provide clinicians with the ability to directly adjust the plasma levels of HLCD to the point of therapeutic tolerance by controlling the dose and the schedule of drug administration. The inventors contend that this should lead to a superior ability to achieve more effective antitumor activity and reduced interpatient variability of the plasma levels of HLCD.

The different observations made in these studies suggest that direct administration of HLCD by parenteral and oral administration could provide significant clinical benefit for patients undergoing treatment for cancer. However, in the past, HLCD have been considered insufficiently water soluble for clinical use. The current invention overcomes the solubility problem by providing lactone stable pharmaceutically acceptable formulations of HLCD which upon dilution with an acceptable parenteral vehicle gives a stable solution of useful concentrations of HLCD for parenteral use and also a concentrated solution or suspension of HLCD suitable for encapsulation within a gelatin capsule for oral HLCD formulations.

SUMMARY OF THE INVENTION

This invention involves the pharmaceutical formulation of lactone stable highly lipophilic camptothecin derivatives ("HLCD") to treat cancer in humans. Also within the scope of the present invention is a stable HLCD solution or suspension in NMP (1-Methyl-2-Pyrrolidinone, defined above) which, upon dilution with suitable parenteral vehicle, provides a final infusion containing a HLCD activity in the range of about 0.001 mg to about 1.0 mg per ml. The present invention also relates to a highly concentrated solution or suspension of HLCD in the range of about 1.0 mg to about 40.0 mg per ml in NMP suitable for encapsulation within a gelatin capsule. For the purposes of this invention, lactone stable HLCD is defined as any A- and/or B-ring substituted camptothecin derivative (HLCD) having a water solubility of less than 5 micrograms per milliliter of water in the lactone form.

For the purpose of this invention, a highly lipophilic camptothecin derivative ("HLCD"), having a water solubility of 5 micrograms per milliliter or less, has the general structural formula:

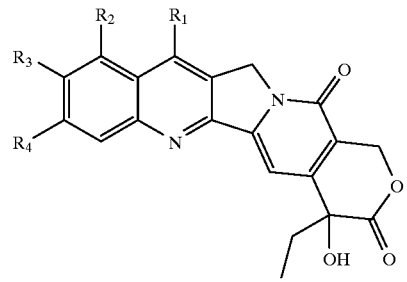

wherein $R_1$, $R_2$, $R_3$, $R_4$=H, lower alkyl, alkoxy, acyloxy, hydroxy, acyl, halo, amido, or cyano group;

wherein $R_1$ and $R_2$ together may represent —$X_1$—$X_2$—$X_3$— and wherein $X_1$, $X_2$, $X_3$ may be $CR_5R_6$, O, S or $NR_7$; and wherein $R_5$, $R_6$, $R_7$=H, lower alkyl, alkoxy, acyloxy, hydroxy, acyl, halo, amido, or cyano group;

wherein $R_2$ and $R_3$ together may represent —$X_1$—$X_2$—$X_3$— and wherein $X_1$, $X_2$, $X_3$ may be $CR_5R_6$, O, S or $NR_7$; and wherein $R_5$, $R_6$, $R_7$=H, lower alkyl, alkoxy, acyloxy, hydroxy, acyl, halo, amido, or cyano group;

wherein $R_3$ and $R_4$ together may represent —$X_1$—$X_2$—$X_3$— and wherein $X_1$, $X_2$, $X_3$ may be $CR_5R_6$, O, S or $NR_7$; and wherein $R_5$, $R_6$, $R_7$=H, lower alkyl, alkoxy, acyloxy, hydroxy, acyl, halo, amido, cyano group;

Another embodiment of this invention is an injectable, sterile solution comprising N-methyl-2-pyrrolidinone and a highly lipophilic camptothecin derivative ("HLCD") having a water solubility of 5 micrograms per milliliter or less, with the general structural formula:

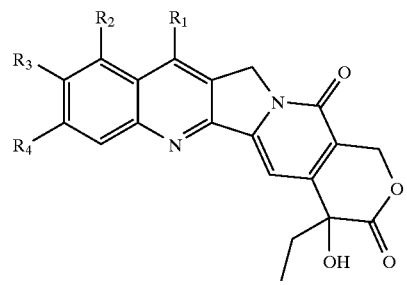

wherein $R_1$, $R_2$, $R_3$, $R_4$=H, lower alkyl, alkoxy, acyloxy, hydroxy, acyl, halo, amido, or cyano group;

wherein $R_1$ and $R_2$ together may represent —$X_1$—$X_2$—$X_3$— and wherein $X_1$, $X_2$, $X_3$ may be $CR_5R_6$, O, S or $NR_7$ and wherein $R_5$, $R_6$, or $R_7$=H, lower alkyl, alkoxy, acyloxy, hydroxy, acyl, halo, amido, or cyano group;

wherein $R_2$ and $R_3$ together may represent —$X_1$—$X_2$—$X_3$— and wherein $X_1$, $X_2$, $X_3$ may be $CR_5R_6$, O, S or $NR_7$ and wherein $R_5$, $R_6$, or $R_7$=H, lower alkyl, alkoxy, acyloxy, hydroxy, acyl, halo, amido, or cyano group; and wherein $R_3$ and $R_4$ together may represent —$X_1$—$X_2$—$X_3$— and wherein $X_1$, $X_2$, $X_3$ may be $CR_5R_6$, O, S or $NR_7$ and wherein $R_5$, $R_6$, or $R_7$=H, lower alkyl, alkoxy, acyloxy, hydroxy, acyl, halo, amido, or cyano group.

A further embodiment of this invention is a pharmaceutically acceptable acid selected from the group consisting of acetic acid, citric acid, fumaric acid, maleic acid, ascorbic acid, hydrochloric acid, phosphoric acid, gluconic acid, lactic acid, and hydrochloric acid may also be added to the above defined injectable sterile solution. For the purposes of this invention, a pharmaceutically acceptable acid is defined as an acid selected from the group consisting of, but not limited to, acetic acid, citric acid, fumaric acid, maleic acid, ascorbic acid, hydrochloric acid, phosphoric acid, gluconic acid, lactic acid, and hydrochloric acid.

Additionally, the above injectable sterile solution may also include one or more excipients including, for example, but not limiting to, ethanol, benzyl alcohol, glycerin, polaxomer, PEG-300, PEG-400, Tween-80, Cremaphor or taurocholic acid or a pharmaceutically acceptable salt thereof.

For the purpose of this invention, one of ordinary skill in this art would know that the A-ring is the first ring on the left side of the above chemical structure and that the B-ring is the second from the left ring of the above structure. Additionally, one of ordinary skill in this art knows that R-1 in the above chemical structure is also defined as position 7 of the B-ring. R-2 in the above chemical structure is also defined as position 9 of the A-ring. R-3 in the above chemical structure is also defined as position 10 of the A-ring and R-4 in the above chemical structure is also defined as position 11 of the A-ring.

Another embodiment of this invention is substitutions in only the A-ring of the above structure only, substitutions in only the B-ring only and also substitutions in both the A-ring and the B-ring. Examples of HLCD A-ring substituted camptothecin derivative include, but are not limited to, substitutions at positions 9, 10, or 11 and combinations thereof. For example, A-ring substitutions could be at position 9 only, at position 10 only, at position 11 only, as well as A-ring substitutions at positions 9 and 10, at positions 9 and 11, and at positions 9, 10, and 11. Additionally, B-ring substituted camptothecin derivatives include, but are not limited to, substitutions at position 7. This invention also embodies substitutions in both the A-ring and in the B-ring. For example, this invention includes substitutions at positions 7 and 9, at positions 7 and 10, at positions 7 and 11, at positions 7, 9, 10, and 11 and at positions 7, 10, and 11. The above substitutions are examples only and do not intend to limit the instant invention to the substitutions listed.

Examples of HLCD (any A- and/or B-ring substituted camptothecin derivative) as defined in the instant invention include, without restriction or limitation, 10,11-methylenedioxy camptothecin, 10,11-ethylenedioxy camptothecin, 7-ethyl camptothecin, 7-ethyl-10-hydroxy camptothecin, 9-methyl camptothecin, 9-chloro-10,11-methylenedioxy camptothecin, 9-chloro camptothecin, 10-hydroxy camptothecin, 9,10-dichloro camptothecin, 10-bromo camptothecin, 10-chloro camptothecin, 9-fluoro camptothecin, 10-methyl camptothecin, 10-fluoro camptothecin, 9-methoxy camptothecin, and 11-fluoro camptothecin.

Direct administration of HLCD to human patients with cancer is likely to offer several important clinical advantages over administration of more water soluble camptothecin derivatives such as SCPT, CPT-11, topotecan, 9-amino camptothecin, 9-nitro camptothecin and 7-(4-methylpiperazinomethylene)-10,11-ethylenedioxy camptothecin.

For example:

(1) direct administration of HLCD allows the clinician to tailor the administration of the active cytoxic species (lactone stable form of HLCD) to suit the patient's tolerance;

(2) direct administration of HLCD overcomes interpatient variability which may be due to polymorphism of key enzyme(s) in the metabolism of CPT-11 to 7-ethyl-10-hydroxy camptothecin;

(3) clinicians can more consistently optimize the drug dosage and schedule to achieve the maximum tolerated dose of HLCD which is likely to lead to the most beneficial clinical anti-cancer effect; and (4) direct administration of an HLCD in the lactone form will have a generally superior ability to penetrate tissue than the direct administration of water soluble camptothecin derivatives in the lactone stable or carboxylate forms.

Regarding the clinical utility of lactone stable pharmaceutical formulations of HLCD for the treatment of human cancer, this invention provides the following:

(1) solutions and suspensions comprising lactone stable HLCD;

(2) formulations of lactone stable HLCD suitable for parenteral administration;

(3) oral formulations of lactone stable HLCD; and (4) use of formulations of HLCD for the treatment of localized complications of cancer by direct administration via instillation into various body cavities.

HLCD Dissolved or Suspended in N-Methyl-2-Pyrrolidinone With or Without Additional Excipients Another embodiment of the claimed invention is a highly lipophilic camptothecin derivative (HLCD) solution or suspension containing HLCD and N-methyl-2-pyrrolidinone ("NMP"). Yet another embodiment of the claimed invention is a highly lipophilic camptothecin derivative (HLCD) solution or suspension containing HLCD, N-methyl-2-pyrrolidinone ("NMP") and a pharmaceutically acceptable acid.

There are many pharmaceutically acceptable acids for this invention, but the inventors prefer to select one from the group consisting of acetic acid, citric acid, fumaric acid, maleic acid, ascorbic acid, hydrochloric acid, phosphoric acid, gluconic acid, lactic acid, and hydrochloric acid.

Taurocholic acid, a bile acid with very weak acidic properties may be used for certain oral formulations if desired, and is not incorporated in any formulation for the purpose of lowering the pH of the formulation. Also for the purposes of this invention, the term "pharmaceutically acceptable" is defined as a reference to the high degree of physiologic safety of the liquid organic excipients contained within the undiluted formulations when administered to human patients in the amounts contained within a range of 1 to 50 milliliter volumes administered to humans patients for one to five consecutive days.

One of the key discoveries in the present invention is the unexpectedly high solubility of HLCD in N-methyl-2-pyrrolidinone (NMP). N-Methyl-2-pyrrolidinone is an organic liquid excipient and is also known as 1-methylpyrrolidinone, N-methyl-2-pyrrolidinone, 1-methyl-5-pyrrolidinone, methylpyrrolidinone, N-methyl pyrrolidinone, methylpyrrolidinone, N-methylpyrrolidone, N-methyl-2-pyrrolidone, M-pyrol, and NMP.

NMP exhibits a high degree of physiologic safety in mammals with the following LD50 values: (rat) oral—7000 mg/kg, intraperitoneal—2472 mg/kg, intravenous—2266 mg/kg, (mice) oral—7725 mg/kg, intraperitoneal—4429 mg/kg, intravenous—3605 mg/kg, (rabbit) skin—8000 mg/kg (Registry of Toxic Effects of Chemical Substances, 1983–84 Supplement, Page 1628). NMP has been used to formulate etoposide (Etoposide, U.S. Pat. No. 4,772,589) and acridine derivatives (M-AMSA, U.S. Pat. No. 5,034, 397). Etoposide and acridine derivatives (1) are anticancer drugs; (2) are chemically unrelated to HLCD; (3) are more water soluble than HLCD; and (4) exert their antitumor effects by vastly different mechanisms than HLCD.

NMP has also been used for oral formulations of the antibiotic clarithromycin (Clarithromycin, WO patent #9,014,094) and other drugs. NMP is a key excipient of the instant invention which allows an exceptionally high degree of drug solubility of HLCD (range 1 mg/ml to 40 mg/ml)in NMP as a solution or suspension. An HLCD solution comprising NMP with or without other combinations of excipients described herein, which can be diluted with a parenteral vehicle such as sterile injectable water USP, 5% Dextrose solution for injection USP or 0.9% sodium chloride solution for injection USP, such that the amount of HLCD dissolved in the diluted infusion is from about 0.001 mg/ml to about 1.0 mg/ml, is taught in the present invention. The inventors have discovered that HLCD show remarkably high solubility in NMP compared to other common pharmaceutical solvents such as water, ethanol, benzyl alcohol, propylene glycol, PEG 300, PEG 400, dimethylisosorbide or dimethylacetamide (Table 5). This high solubility of HLCD in NMP makes NMP a unique and highly useful pharmaceutical solvent for making useful solutions or suspensions of HLCD.

TABLE 5

Solubility of Camptothecin in Various Solvents

| Solvent | Concentration, mg/ml |
|---|---|
| Milli-Q Water | 0.0002 |
| Ethanol | 0.051 |
| Benzyl alcohol | 1.674 |
| Propylene glycol | 0.281 |
| PEG 300 | 0.706 |
| Dimethylisosorbide | 0.928 |
| Dimethylacetamide | 5.000 |
| N-Methyl-2-pyrrolidinone (NMP) | >15.000 (range 15–20) |

NMP is inert with respect to undesirable chemical reactions with HLCD and is therefore a highly useful excipient to create solutions of HLCD in the lactone form. Further utility of NMP in the present invention is the discovery that NMP allows the introduction of additional excipients which further improve the overall utility of the HLCD dissolved in the NMP solution in a manner which are of additional benefit for parenteral or oral administration to human patients with cancer. The HLCD solution or suspension is prepared by mixing the desired components with NMP and adding a pharmaceutically acceptable acid to adjust the pH to 3–5.

A pharmaceutically acceptable acid is preferably included in the NMP solutions and suspensions of the present invention. Any pharmaceutically acceptable acid may be used; for example mineral acids such as hydrochloric acid or phosphoric acid; and carboxylic acids such as tartaric, lactic, ascorbic, gluconic, citric, succinic, fumaric, or maleic acids. Hydrochloric acid, phosphoric acid and carboxylic acids are the most preferred for the novel oral and parenteral formulations described in the present invention. The amount of acid used may be from about 100 to about 5000 parts by weight of acid per part by weight of HLCD and preferably from about 1000 to 2500 parts by weight of acid per part by weight of HLCD. Citric acid is preferably used in a proportion of from about 1000 to about 2000 parts by weight. Oral formulations of NMP and HLCD can additionally contain taurocholic acid. The NMP HLCD solution is miscible with ethanol, benzyl alcohol, polysorbate-80 (Tween-80), polyethylene glycol (PEG), polyoxyethylated castor oil, propylene glycol, isopropyl myristate, corn oil, cottonseed oil, and the like.

An object of the present invention is to provide a solution or suspension of HLCD in the lactone form in NMP. A more concentrated HLCD-NMP solution or suspension (10 mg or more per milliliter of solution or suspension) is particularly useful as a filling solution or suspension for gelatin capsules. A HLCD-NMP solution may also be formulated for parenteral administration providing a useful and practical means to dissolve the drug.

The present invention is prepared by mixing HLCD in NMP alone or by subsequent addition of additional excipients including or excluding any combination the following: (a) a carboxylic acid and/or mineral acid, (b) polyethylene glycol (PEG-300 and/or PEG-400), (c) alcohol (ethyl and/or benzyl alcohol) (d) polysorbate-80 (Tween-80) and (e) taurocholic acid. The amount of HLCD contained in the solution or suspension described in this invention is not specifically restricted but may be any amount convenient for pharmaceutical purposes, and may be selected according to the dosage to be prepared. A preferred capsule filling solution or suspension contains from about 1 mg to about 40 mg of HLCD activity per ml of solution or suspension.

Another preferred embodiment of the claimed invention is an HLCD solution or suspension prepared by dissolving or suspending the desired components in NMP in the presence of a pharmaceutically acceptable acid.

In the formulations provided by the instant invention, the HLCD is soluble or suspended and maintained in its active lactone form. The non-enzymatic conversion of the pH labile E-ring from the closed lactone (active) to the open carboxylate form (inactive) is reduced by formulating HLCD under acidic pH conditions (pH range of 3 to 5). Thus, an acid is included by the inventors to assure that an acidic pH value is maintained upon dilution to form a micellar solution or suspension. Examples of preferred carboxylic acids effective in this invention include citric, gluconic, lactic, maleic, tartaric, or ascorbic acids. Other acids such as hydrochloric acid and phosphoric acid can be employed instead or in addition to citric acid to form the most preferred solution.

Yet another embodiment of the claimed invention is that the solution or suspension of HLCD contains from about 1.0 mg to about 40.0 mg activity of HLCD per ml of solution or suspension. This concentration of HLCD in the resulting formulation solution or suspension would be useful and effective for both oral and parenteral administration of the HLCD to human patients with cancer.

When oral dosages are to be administered in a capsule form, it is advantageous to have a concentrated solution or suspension of HLCD suitable for encapsulation within a soft or hard gelatin capsule. Concentrated solutions or suspensions allow the preparation of capsules of smaller size which allows easier ingestion by the patient, and may also reduce the number of capsules to be swallowed. These factors are important in view of the generally poor condition of cancer patients.

Taurocholic acid, a bile acid, may enhance in the intestinal absorption of the drug in certain patients. The present invention takes advantage of the discovery that taurocholic acid, or a pharmaceutically acceptable salt thereof, when included with HLCD in a solution or suspension dosage composition, results in improved absorption of the drug following oral ingestion of the composition. It is believed that this is due to the formation of a micellar solution of HLCD on dilution thereof with the gastric contents.

The phenomenon of micellar solubilization of poorly water-soluble drugs mediated by bile acids, including taurocholic acid, has been previously reported with respect to glutethimide, hexesterol, griseofulvin (Bates et al.), reserpine (Malone et al.) and fatty acids and cholesterol (Westergaard et al.). The use of taurocholic acid or a pharmaceutically acceptable salt thereof in the present invention involves a pharmaceutical solution of HLCD which has the useful property of providing a stable apparent solution of the drug upon dilution thereof with from 1 to 100 volumes of water. The solution is stable and free of precipitate for a period of at least two hours; sufficient time to permit administration and absorption by the patient.

It has been observed with similar solutions of etoposide, which is a chemically different anticancer drug, that the bioavailability of the drug following oral administration is substantially equivalent to that achieved by intravenous administration of a solution of the chemically unrelated anticancer drug etoposide (U.S. Pat. No. 4,713,246). Analogous to that of etoposide, it is believed that ingestion of the present dosage form of HLCD and resulting dilution thereof by the stomach contents, results in the formation of a micellar solution of HLCD in the stomach which is readily absorbed by the gastrointestinal tract. However, the Applicants do not wise to be bound by any theoretical explanation of the mechanism by which the superior oral bioavailability of the present HLCD formulation is achieved.

Antitumor Compositions Comprising HLCD

Yet another preferred embodiment of the claimed invention is an antitumor composition comprising a solution or suspension of a HLCD dissolved or suspended in NMP or NMP containing from about 1.0 mg to about 40.0 mg HLCD activity per milliliter of solution or suspension and containing from about 100 to about 5000 parts of a pharmaceutically acceptable carboxylic acid or hydrochloric acid, or phosphoric acid per part by weight of HLCD. The inventors prefer to use 1000 to 2000 parts by weight of a pharmaceutically acceptable carboxylic acid and/or mineral acid per part by weight of HLCD. For the purpose of this invention, examples of carboxylic acid that can be used in this invention are tartaric, lactic, ascorbic, gluconic, citric, succinic, fumaric, or maleic acids and examples of mineral acids useful in this invention are hydrochloric acid or phosphoric acid.

Another embodiment of this invention is an antitumor composition comprising of a solution or suspension of HLCD dissolved or suspended in NMP in the presence of a pharmaceutically acceptable acid, wherein said solution or suspension further comprises polyethylene glycol.

Another embodiment of this invention is an antitumor composition comprising a solution or suspension of HLCD dissolved in NMP in the presence of a pharmaceutically acceptable acid, wherein said solution or suspension further comprises polyethylene glycol and ethyl alcohol or benzyl alcohol or the solution or suspension further comprises ethyl alcohol and benzyl alcohol.

Another embodiment of this invention is an antitumor composition comprising a solution or suspension of HLCD dissolved or suspended in NMP in the presence of a pharmaceutically acceptable acid, wherein said solution or suspension further comprises polyethylene glycol, and polysorbate-80.

Another embodiment of this invention is an antitumor composition comprising a solution or suspension of HLCD dissolved in NMP in the presence of a pharmaceutically acceptable acid, wherein said solution or suspension further comprises polyethylene glycol, ethyl alcohol or benzyl alcohol (or ethyl alcohol and benzyl alcohol) and polysorbate-80.

Another embodiment of this invention is an antitumor composition comprising a solution or suspension of HLCD dissolved or suspended in NMP in the presence of a pharmaceutically acceptable acid, wherein said solution or suspension further comprises polyethylene glycol, polysorbate-80 and taurocholic acid or a pharmaceutically acceptable salt thereof.

Yet another embodiment of this invention is wherein the solution or suspension of antitumor composition contains for each part by weight of HLCD, 1,000–10,000 parts by weight of NMP, 100–5,000 parts by weight of a pharmaceutically acceptable acid, 1–10 parts by weight of taurocholic acid or a pharmaceutically acceptable salt thereof, 1,000–10,000 parts by weight of polyethylene glycol (PEG-300 and/or PEG-400). An additional embodiment is wherein said acid is an carboxylic acid and the inventors prefer citric acid.

Another embodiment of the claimed invention is the antitumor composition further comprising a lower alcohol. Many different alcohols would be effective in this invention, but the inventors prefer to use ethanol or a combination of ethanol and benzyl alcohol. Another embodiment of the claimed invention is an antitumor composition further comprised of glycerin as a co-solvent.

Yet another embodiment of this invention is an antitumor composition comprising a solution or suspension of HLCD dissolved or suspended in NMP in the presence of a pharmaceutically acceptable acid preferably citric acid and or hydrochloric or phosphoric acid, polyethylene glycol (PEG-300 and/or PEG-400), polysorbate-80, ethanol, and glycerin.

An additional embodiment of this invention is wherein said solution or suspension contains for each part by weight of HLCD, 1,000–10,000 parts by weight of NMP, 1,000–5,000 parts by weight of a pharmaceutically acceptable acid, 1–10 parts by weight of taurocholic acid or a pharmaceutically acceptable salt thereof, 1,000–10,000 parts by weight of polyethylene glycol, 0.1–2.0 parts by weight of glycerin, 1,000–5,000 parts by weight of ethanol.

Yet another embodiment of this invention is an antitumor composition comprising a solution or suspension of HLCD dissolved or suspended in NMP in the presence of a pharmaceutically acceptable acid, wherein said solution or suspension further comprises ethyl alcohol or ethyl alcohol and benzyl alcohol, and polyethylene glycol.

As a more preferred embodiment for this antitumor composition, the pharmaceutically acceptable acid is citric acid, the polyethylene glycol is PEG-400, the lower alcohol is ethanol and the surfactant is polysorbate-80.

Another embodiment of this invention, is an antitumor composition comprising a solution or suspension of about 1.0 mg to about 150.0 mg of HLCD dissolved or suspended in 1,000–10,000 parts by weight of NMP in the presence of about 100 to 5000 parts by weight of a pharmaceutically acceptable organic carboxylic acid. This antitumor composition further comprises about 1,000–10,000 parts by weight of polyethylene glycol, about 1,000 to 5,000 parts of a pharmaceutically acceptable alcohol.

More preferred for this antitumor composition is when the acid is citric acid, the polyethylene glycol is PEG-400, the alcohol is ethanol and the surfactant is polysorbate-80.

Another embodiment of this invention is an antitumor composition comprising a solution or suspension about 1.0 mg to about 150.0 mg of HLCD dissolved or suspended in 1,000 to 10,000 parts of NMP in the presence of 100 to 5,000 parts of a pharmaceutically acceptable carboxylic acid. This solution or suspension further comprises about 1,000 to 5,000 parts of a pharmaceutically acceptable alcohol 1,000 to 10,000 part of polyethylene glycol, and 1,000 to 10,000 parts of polysorbate-80.

More specifically for this antitumor composition, the acid is citric acid, the alcohol is ethanol, and the polyethylene glycol is PEG-400.

Another embodiment of this invention is an antitumor composition comprising a solution or suspension of 1.0 mg to about 150.0 mg of HLCD dissolved or suspended in 1,000 to 10,000 parts of NMP, wherein this solution or suspension further comprises about 1,000 to 10,000 parts polyoxyethylated castor oil, about 1,000 to 5,000 parts by weight ethyl alcohol, and about 1,000 to 5,000 parts citric acid, 1,000 to 10,000 parts of polyethylene glycol, and 1,000 to 10,000 parts of polysorbate-80.

In a more preferred embodiment, HLCD is solubilized or suspended in a manner suitable for clinical use by forming a solution or suspension of 1.0 to 40.0 mg of HLCD per 1 ml in a vehicle comprising 1,000 to 10,000 parts by weight of NMP, ethyl alcohol 1,000 to 5,000 parts by weight, benzyl alcohol-1,000 to 5,000 parts by weight, citric acid 1,000 to 5,000 parts by weight, polyethylene glycol (PEG-300 or PEG-400) 1,000 to 10,000 parts by weight, and polysorbate-80 (Tween-80) 1,000 to 10,000 parts. While either polyethylene glycol (PEG-300 or PEG-400) would be effective in this embodiment, the inventors prefer to employ PEG-400.

This preferred embodiment of a HLCD composition is summarized in Table 6 as follows:

TABLE 6

COMPONENT PARTS BY WEIGHT FOR PARENTERAL OR ORAL FORMULATIONS OF HLCD

| Ingredients | Parts by weight |
|---|---|
| HLCD | 1.0 to 40.0 |
| (1)EtOH | 1,000 to 5,000 |
| (1)Benzyl Alcohol | 1,000 to 5,000 |
| Acid | 100 to 5,000 |
| PEG 400 | 1,000 to 10,000 |
| NMP | 1,000 to 10,000 |
| (1)Cremaphor-EL | 1,000 to 10,000 |
| (2)Glycerin | 0.5 to 2.5 |
| (2)Taurocholic Acid | 1 to 10 |
| Polysorbate 80 (Tween-80) | 1,000 to 10,000 |

(1)optional additions individually or in any combination to oral or parenteral HLCD formulations
(2)used in oral formulations only Another more preferred parenteral formulation comprises HLCD formulated for dilution prior to parenteral administration made of 1 to 40 mg of HLCD in 1 ml of solvents including 1,000 to 10,000 parts by weight of HLCD of Cremaphor EL (polyoxyethylated castor oil), 1,000 to 5,000 parts ethyl alcohol, NMP 1,000 to 10,000 parts, and citric acid 1,000 to 5,000 parts.

Yet another embodiment of this invention for oral administration to a patient with cancer is the HLCD dissolved or suspended in NMP in the presence of a pharmaceutically acceptable acid.

A further embodiment of this invention is the claimed composition and method of administering the composition by encapsulating the claimed formulations within a hard gelatin capsule. Yet another embodiment of the claimed composition and method of administering the composition is encapsulating the claimed formulations within a soft gelatin capsule or hard gelatin capsule. One of ordinary skill in the art will know that any of the claimed formulations adapted for oral administration can be used as the fill for the soft or hard gelatin capsule.

A more specific embodiment of the claimed invention is an oral formulation of HLCD in hard or soft gelatin capsules (comprised of gelatin/glycerin/sorbitol/purifiers) containing 1.0 to 40.0 mg of HLCD per milliliter in a solution or suspension comprising citric acid 1,000 to 5,000 parts by weight, glycerin 0.5 to 2.5 parts by weight, polyethylene glycol (molecular weight 300 to 400) 1,000 to 10,000 parts by weight, ethyl alcohol 1,000 to 5,000 parts by weight, PEG-400 1,000 to 10,000 parts by weight, polysorbate-80 1,000 to 10,000 parts by weight, and 1,000 to 10,000 parts NMP.

Another preferred oral formulation will include the addition of taurocholic acid 1 to 10 parts by weight. The soft gelatin capsules may also be composed of any of a number of compounds used for this purpose including, for example, a mixture of gelatin, glycerin, sorbitol, and parabens.

Table 7 below indicates parts by weight of different components to be included in the oral formulation to be administered in capsules. Several components are marked with an "**" which denotes that the components are "optional." For the purpose of this invention, inclusion of these components depends on a variety of different factors; i.e. type of cancer the patient has, pretreated previously, etc.

TABLE 7

COMPONENT PARTS BY WEIGHT FOR ORAL FORMULATION OF HLCD

| Ingredients | Parts by Weight |
|---|---|
| HLCD | 1 to 40 |
| NMP | 1,000 to 10,000 |
| Citric Acid | 1,000 to 5,000 |
| EtOH | 1,000 to 5,000 |
| Polysorbate-80 (Tween-80) | 1,000 to 10,000 |
| PEG-400 | 1,000 to 10,000 |
| Glycerin** | 0.5 to 2.5 |
| Taurocholic Acid** | 1 to 10 |

Clinicians will administer HLCD in these formulations to human patients with cancer according to schedules which maximize its potential antitumor effects and diminish its potential toxic side effects. Except at extremely high doses which produce high plasma concentrations of the drug, the antitumor activity of HLCD can be increased by increasing the duration of exposure (time dependent) rather than increasing the dose (dose dependent) of the drug. Increased antitumor effects associated with increasing the duration of exposure is most likely related to the predominant S-phase mode of antitumor activity of HLCD. HLCD are S-phase-active agents therefore, the greatest antitumor effect in humans will likely be observed with prolonged infusion or closely spaced repetitive administration schedules. Such schedules of administration would expose more cycling tumor cells to the drug and increase the frequency of exposure of the tumor cells in S-phase to sufficiently toxic levels of the drug.

A further embodiment of this invention is that the claimed HLCD antitumor composition can be used to treat a variety of different cancer types. The claimed formulations and compositions of this invention may be used in treatment of a number of tumors (cancers) including, without limitation, human cancers of the lung, breast, colon, prostate, melanoma, pancreas, stomach, liver, brain, kidney, uterus, cervix, ovaries, and urinary tract.

In many cases, the site and type of tumor to be treated will influence the preferred route of administration and therapeutic regimen to be applied. Consequently, although the formulations of the invention may be most usually administered by intravenous injection, infusion or orally, these formulations may also can be delivered directly into the tumor site or by other methods designed to target the drug directly to the tumor site. For example, in patients with malignant pleural effusion, the intrapleural route may be preferred; in patients with poor venous access the subcutaneous route of administration may be preferred; in patients with primary or metastatic cancer involving the brain or nervous system, the intracisternal or intrathecal route of administration may be most advantageous; in patients with malignant ascites secondary to cancer, one may select intraperitoneal administration; and in patients with bladder cancer direct intravesicular instillation may be most advantageous. Similarly, in tumors of the skin, the formulation may be topically applied. An oral formulation is also taught for use where suitable for patients taking the medication outside of the hospital or clinic.

An additional embodiment of this invention is a HLCD solution or suspension comprising HLCD dissolved or suspended in NMP, in the presence of a pharmaceutically acceptable acid and this solution or suspension is prepared for oral, intrapleural, intrathecal, subcutaneous, intracisternal, intravesicular, intraperitoneal, topical or intravenous administration to a patient with cancer.

A further embodiment of claimed HLCD is a method of treatment of cancer in humans with convergent therapy or combination therapy. This method uses HLCD dissolved in NMP, in the presence of pharmaceutically acceptable acid and co-administers it with additional drugs selected from the group consisting of, but not limited to, carmustine, azathioprine, cis-platinum, carboplatin, iproplatin, cyclophosphamide, ifosfamide, etoposide, ara-C, doxorubicin, daunorubicin, nitrogen mustard, 5-fluorouracil, bleomycin, mitomycin-C, fluoxymesterone, mechlorethamine, teniposide, hexamethylmelamine, leucovorin, melphelan, methotrexate, mercaptopurine, mitoxantrone, BCNU, CCNU, procarbazine, vincristine, vinblastine, vindesine, thioTEPA, amsacrine, G-CSF, GM-CSF, erythropoietin, γ-methylene-10-deazaaminopterin or γ-methylene-10-ethyl-10-deazaaminopterin, taxol, and 5-azacytidine. For the purpose of this invention, the terms convergent, co-administered, and combination are used interchangeably.

HLCD dissolved or suspended in NMP with or without the described combination of other formulation excipients that have been taught in the foregoing section have additional utility when administered parenterally using a prolonged schedule of administration. To increase the utility of HLCD for parenteral infusions, the HLCD parenteral compositions may be diluted with an appropriate volume of an aqueous vehicle to a concentration of about 0.001 mg/ml to 1.0 mg/ml of HLCD activity.

A further embodiment of the claimed invention is a solution of any of the claimed HLCD compositions and formulations for administration to a patient with cancer upon dilution with a sterile aqueous parenteral vehicle. For the purposes of this invention, parenteral aqueous vehicles suitable for dilution include dextrose 5 to 10% in water, 0.9% NaCl in water with or without 5% or 10% Dextrose, 0.45% NaCl in water with or without 5% or 10% Dextrose, Lactated Ringer's Solution, 3% NaCl in water with or without 5% to 10% Dextrose, water USP for injection or sterile lipid formulations, such as intralipid, used for parenteral nutritional support for cancer patients.

This invention is also directed to a solution or suspension comprising an A-ring substituted camptothecin having a water solubility of 5 micrograms or less than 5 micrograms per milliliter wherein the substituted camptothecin is dissolved or suspended in an effective amount of N-methyl-2-pyrrolidinone. A-ring substitutions include any substitutions on the A-ring but the inventors prefer to employ substitutions at position 9, 10 or 11 of the A-ring.

This invention is also directed to a solution or suspension comprising an B-ring substituted camptothecin having a water solubility of 5 micrograms or less than 5 micrograms per milliliter wherein the substituted camptothecin is dissolved or suspended in an effective amount of N-methyl-2-pyrrolidinone. B-ring substitutions include any substitutions on the B-ring but the inventors prefer to employ substitutions at position 7 of the B-ring.

This invention is also directed to a solution or suspension comprising a substituted camptothecin having a water solubility of 5 micrograms or less than 5 micrograms per milliliter wherein the camptothecin has substitutions on the A-ring and on the B-ring and wherein the substituted camptothecin is dissolved or suspended in an effective amount of N-methyl-2-pyrrolidinone. This invention includes substitutions at all possible locations on the A- and B-ring but the inventors prefer substitutions at position 7 of the B-ring and at positions 9, 10, and/or 11 of the A-ring.

This invention is also directed to a solution or suspension comprising an B-ring substituted camptothecin having a water solubility of 5 micrograms or less than 5 micrograms per milliliter wherein the substituted camptothecin is dissolved or suspended in an effective amount of N-methyl-2-pyrrolidinone.

All of the embodiments outlined below apply to A-ring substituted camptothecins, B-ring substituted camptothecins and to substituted camptothecins containing both A-ring and B-ring substitutions. For this invention, "dissolved" and "suspended" have regular meanings known to one of ordinary skill in this art.

The above solution or suspension may further contain a pharmaceutically acceptable acid wherein this acid can be a carboxylic acid selected from the group consisting of acetic acid, citric acid, fumaric acid, maleic acid, ascorbic acid, gluconic acid, and lactic acid. The above solution or suspension may further contain a pharmaceutically acceptable acid wherein this acid can be a mineral acid selected from a group consisting of hydrochloric acid and phosphoric acid. Additionally, the pharmaceutically acceptable acid in the above solution or suspension may be selected from the group consisting of acetic acid, citric acid, fumaric acid, maleic acid, ascorbic acid, phosphoric acid, gluconic acid, lactic acid, and hydrochloric acid. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above solution or suspension may further contain a lower alcohol selected from the group consisting of ethanol and benzyl alcohol. The above solution or suspension may also contain a polyethylene glycol selected from a group consisting of PEG-300 and PEG-400. And the above solution or suspension may further contain a non-ionic surfactant. The inventors prefer to employ polysorbate-80 (Tween-80) but most surfactants are suitable. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above solution or suspension comprising an A-ring substituted or B-ring substituted or A- and B-ring substituted camptothecin and N-methyl-2-pyrrolidinone may also further contain a polyethylene glycol and a non-ionic surfactant. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

The above solution or suspension comprising an A-ring substituted or B-ring substituted or A- and B-ring substituted camptothecin and N-methyl-2-pyrrolidinone may also contain a lower alcohol, polyethylene glycol and a non-ionic surfactant. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above solution or suspension comprising an A-ring substituted or B-ring substituted or A- and B-ring substituted camptothecin and N-methyl-2-pyrrolidinone may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above solution or suspension comprising an A-ring substituted or B-ring substituted or A- and B-ring substituted camptothecin, N-methyl-2-pyrrolidinone, and acid may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Yet another embodiment of this invention is the above solution or suspension comprising an A-ring substituted or B-ring substituted or A- and B-ring substituted camptothecin, N-methyl-2-pyrrolidinone, acid, and lower alcohol may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Yet another embodiment of this invention is the above solution or suspension comprising an A-ring substituted or B-ring substituted or A- and B-ring substituted camptothecin, N-methyl-2-pyrrolidinone, acid, and polyethylene glycol may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above solution or suspension comprising an A-ring substituted or B-ring substituted or A- and B-ring substituted camptothecin, N-methyl-2-pyrrolidinone, acid, and non-ionic surfactant may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above solution or suspension comprising an A-ring substituted or B-ring substituted or A- and B-ring substituted camptothecin, N-methyl-2-pyrrolidinone, acid, polyethylene glycol and non-ionic surfactant may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above solution or suspension comprising an A-ring substituted or B-ring substituted or A- and B-ring substituted camptothecin, N-methyl-2-pyrrolidinone, acid, polyethylene glycol, non-ionic surfactant and lower alcohol may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above solution or suspension comprising an A-ring substituted or B-ring substituted or A- and B-ring substituted camptothecin and N-methyl-2-pyrrolidinone wherein this solution or suspension contains from about 1.0 mg to about 40.0 mg activity per ml of solution or suspension of the substituted camptothecin having a water solubility of less than 5 micrograms per ml of water. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Yet another embodiment of this invention is an antitumor composition comprising a solution or suspension containing an A-ring substituted camptothecin or containing a B-ring substituted camptothecin or containing both an A-ring substituted and a B-ring substituted camptothecin having a water solubility of 5 micrograms or less than 5 micrograms per milliliter dissolved or suspended in N-methyl-2-pyrrolidinone wherein said composition contains from about 1 mg to about 40 mg camptothecin activity per ml and contains about 1,000 to 10,000 parts by weight of N-methyl-2-pyrrolidinone.

For this invention "substituted camptothecin" applies to substitutions in the A-ring or substitutions in the B-ring or substitutions in both the A-ring and the B-ring. This invention includes substitutions at all possible locations on the A- and B-ring but the inventors prefer substitutions at position 7 of the B-ring and at positions 9, 10, and/or 11 of the A-ring.

The antitumor composition comprising a substituted camptothecin and N-methyl-2-pyrrolidinone may also contain from about 100 to about 5,000 parts by weight of a pharmaceutically acceptable acid per part by weight of the substituted camptothecin.

The antitumor composition comprising a substituted camptothecin, N-methyl-2-pyrrolidinone, and acid may further contain 1,000 to 10,000 parts by weight of polyethylene glycol selected from the group consisting of PEG-300 and PEG-400.

The antitumor composition comprising a substituted camptothecin, N-methyl-2-pyrrolidinone, and acid may further contain a non-ionic surfactant. Many different non-ionic surfactants are available but the inventors prefer to employ polysorbate-80 (Tween-80).

The antitumor composition comprising a substituted camptothecin, N-methyl-2-pyrrolidinone, and acid may further contain a lower alcohol selected from the group consisting of ethanol and benzyl alcohol.

The antitumor composition comprising a substituted camptothecin, N-methyl-2-pyrrolidinone, and acid may further a lower alcohol, polyethylene glycol, and a non-ionic surfactant.

The antitumor composition comprising a substituted camptothecin, N-methyl-2-pyrrolidinone, and acid and further containing a lower alcohol, polyethylene glycol, and a non-ionic surfactant wherein said acid is citric acid, wherein said lower alcohol is selected from the group consisting of ethanol and benzyl alcohol, wherein said polyethylene glycol is selected from the group consisting of PEG-300 and PEG-400, and wherein said surfactant is polysorbate-80.

Another embodiment of this invention is an antitumor composition comprising a solution or suspension containing an A-ring substituted camptothecin or containing a B-ring substituted camptothecin or containing both an A-ring substituted and a B-ring substituted camptothecin having a water solubility of 5 micrograms or less than 5 micrograms per milliliter wherein for each part by weight of substituted camptothecin said solution or suspension contains 1,000 to 10,000 parts N-methyl-2-pyrrolidinone, 100 to 5,000 parts of a pharmaceutically acceptable acid, 1,000 to 10,000 parts by weight of polyethylene glycol, and 1,000 to 5,000 parts of lower alcohol selected from the group consisting of ethanol and benzyl alcohol.

Yet another embodiment of this invention is an antitumor composition comprising a solution or suspension containing an A-ring substituted camptothecin or containing a B-ring substituted camptothecin or containing both an A-ring substituted and a B-ring substituted camptothecin having a water solubility of 5 micrograms or less than 5 micrograms per milliliter wherein for each part by weight of substituted camptothecin said solution or suspension contains 1,000 to 10,000 parts N-methyl-2-pyrrolidinone, 100 to 5,000 parts of a pharmaceutically acceptable acid, 1,000 to 5,000 parts of a lower alcohol, and 1,000 to 10,000 parts of a non-ionic surfactant. This invention also embodies the above antitumor composition wherein the acid is citric acid, wherein the alcohol is ethanol, and wherein the non-ionic surfactant is polysorbate-80.

For this invention "substituted camptothecin" applies to substitutions in the A-ring or substitutions in the B-ring or substitutions in both the A-ring and the B-ring. This invention includes substitutions at all possible locations on the A- and B-ring but the inventors prefer substitutions at position 7 of the B-ring and at positions 9, 10, and/or 11 of the A-ring.

This invention further embodies an injectable, sterile solution comprising N-methyl-2-pyrrolidinone, and a highly lipophilic camptothecin derivative having a water solubility of 5 micrograms per milliliter or less, with the general structural formula:

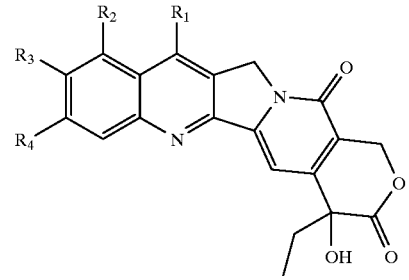

wherein $R_1$, $R_2$, $R_3$, $R_4$=H, lower alkyl, alkoxy, acyloxy, hydroxy, acyl, halo, amido, or cyano group;

wherein $R_1$ nd $R_2$ together may represent —$X_1$—$X_2$—$X_3$— and wherein $X_1$, $X_2$, $X_3$ may be $CR_5R_6$, O, S or $NR_7$ and wherein $R_5$, $R_6$, $R_7$=H, lower alkyl, alkoxy, acyloxy, hydroxy, acyl, halo, amido, or cyano group;

wherein $R_2$ and $R_3$ together may represent —$X_1$—$X_2$—$X_3$— and wherein $X_1$, $X_2$, $X_3$ may be $CR_5R_6$, O, S or $NR_7$ and wherein $R_5$, $R_6$, $R_7$=H, lower alkyl, alkoxy, acyloxy, hydroxy, acyl, halo, amido, or cyano group;

wherein $R_3$ and $R_4$ together may represent —$X_1$—$X_2$—$X_3$— and wherein $X_1$, $X_2$, $X_3$ may be $CR_5R_6$, O, S or $NR_7$ and wherein $R_5$, $R_6$, $R_7$=H, lower alkyl, alkoxy, acyloxy, hydroxy, acyl, halo, amido, or cyano group;

Another embodiment of this invention is the above injectable, sterile solution comprising N-methyl-2-pyrrolidinone, and a highly lipophilic camptothecin derivative further containing a pharmaceutically acceptable acid. This acid may be a carboxylic acid selected from the group consisting of acetic acid, citric acid, fumaric acid, maleic acid, ascorbic acid, gluconic acid, and lactic acid. Or, this acid may be a mineral acid selected from a group consisting of hydrochloric acid and phosphoric acid. The acid may also an acid selected from the group consisting of acetic acid, citric acid, fumaric acid, maleic acid, ascorbic acid, phosphoric acid, gluconic acid, lactic acid, and hydrochloric acid.

Yet another embodiment of this invention is the above injectable, sterile solution comprising N-methyl-2-pyrrolidinone, a highly lipophilic camptothecin derivative, and a pharmaceutically acceptable acid further containing a lower alcohol selected from the group consisting of ethanol and benzyl alcohol.

Yet another embodiment of this invention is the above injectable, sterile solution comprising N-methyl-2-pyrrolidinone, a highly lipophilic camptothecin derivative, and a pharmaceutically acceptable acid further containing a polyethylene glycol selected from a group consisting of PEG-300 and PEG-400.

Yet another embodiment of this invention is the above injectable, sterile solution comprising N-methyl-2-pyrrolidinone, a highly lipophilic camptothecin derivative, and a pharmaceutically acceptable acid further containing a non-ionic surfactant wherein the non-ionic surfactant is polysorbate-80 (Tween-80).

Yet another embodiment of this invention is the above injectable, sterile solution comprising N-methyl-2-pyrrolidinone, a highly lipophilic camptothecin derivative, and a pharmaceutically acceptable acid further containing a polyethylene glycol and a non-ionic surfactant.

Yet another embodiment of this invention is the above injectable, sterile solution comprising N-methyl-2-pyrrolidinone, a highly lipophilic camptothecin derivative, and a pharmaceutically acceptable acid further containing a lower alcohol, polyethylene glycol and a non-ionic surfactant.

Another embodiment of this invention is the above injectable sterile solution comprising an A-ring substituted or B-ring substituted or A- and B-ring substituted camptothecin and N-methyl-2-pyrrolidinone may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above injectable sterile solution comprising an A-ring substituted or B-ring substituted or A- and B-ring substituted camptothecin, N-methyl-2-pyrrolidinone, and acid may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Yet another embodiment of this invention is the above injectable sterile solution comprising an A-ring substituted or B-ring substituted or A- and B-ring substituted camptothecin, N-methyl-2-pyrrolidinone, acid, and lower alcohol may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Yet another embodiment of this invention is the above injectable sterile solution comprising an A-ring substituted or B-ring substituted or A- and B-ring substituted camptothecin, N-methyl-2-pyrrolidinone, acid, and polyethylene glycol may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above injectable sterile solution comprising an A-ring substituted or B-ring substituted or A- and B-ring substituted camptothecin, N-methyl-2-pyrrolidinone, acid, and non-ionic surfactant may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above injectable sterile solution comprising an A-ring substituted or B-ring substituted or A- and B-ring substituted camptothecin, N-methyl-2-pyrrolidinone, acid, polyethylene glycol and non-ionic surfactant may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above injectable sterile solution comprising an A-ring substituted or B-ring substituted or A- and B-ring substituted camptothecin, N-methyl-2-pyrrolidinone, acid, polyethylene glycol, non-ionic surfactant and lower alcohol may also further contain 1 to 10 parts by weight of taurocholic acid or a pharmaceutically acceptable salt thereof. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

Another embodiment of this invention is the above injectable sterile solution comprising an A-ring substituted or B-ring substituted or A- and B-ring substituted camptothecin and N-methyl-2-pyrrolidinone wherein this solution or suspension contains from about 1.0 mg to about 40.0 mg activity per ml of solution or suspension of the substituted camptothecin having a water solubility of less than 5 micrograms per ml of water. Another embodiment of this invention is the above solution or suspension prepared and sterilized for oral, intrapleural, intrathecal, intracisternal, intravesicular, intraperitoneal, topical or intravenous administration to a patient with cancer. Yet another embodiment of this invention is this solution or suspension is encapsulated within a hard gelatin capsule or a soft gelatin capsule.

DESCRIPTION OF THE PREFERRED EMBODIMENTS

In its preferred embodiments, this invention involves preparation and use of novel HLCD solutions or suspensions as described below.

EXAMPLES

The following examples illustrate selected modes for carrying out the claimed invention and are not to be construed as limiting the specification and claims in any way. These examples are provided so as to enable those in ordinary skill in the art to make the compositions of this invention. These examples are not intended to limit the scope of what the inventors regard as the invention. Efforts have been made to ensure accuracy with respect to numbers used to characterize the measured conditions; however, some experimental errors and deviations may be present.

Maintaining an acidic pH (3 to 5) in the HLCD solution or suspension is particularly important to reduce the slow conversion of HLCD lactone to the E-ring-hydrolyzed carboxylate, which occurs at physiological pH. At equilibrium under physiologic pH, the ratio of the open-ring (carboxylate) form to lactone species increases. Hydrolysis of the HLCD lactone ring will be substantially reduced if the drug is kept in an acidic environment. Some of the unpredictable toxicity seen in earlier clinical trials using SCPT may have been due to the in vivo formation of greater amounts of the lactone form of camptothecin, which is 10-fold more toxic than SCPT in mice. The lactone form of HLCD, as in camptothecin, is less water soluble than the carboxylate E-ring form. When early clinical trials were first conducted with camptothecin using sodium hydroxide, the significance of maintaining the closed lactone ring for uniform efficacy and safety in treating patients with cancer was poorly understood. The early reported unpredictable clinical toxicities associated with camptothecin administration may have been exacerbated by the sodium hydroxide formulation which promotes the formation of the carboxylate form, and by the relative lack of understanding of the significance of the lactone form of camptothecin as it relates to antitumor activity.

Example 1

HIGHLY LIPOPHILIC CAMPTOTHECIN DERIVATIVE-NMP FORMULATION FOR INJECTION OR INFUSION

For injection or infusion into aqueous body fluids, a formulation contains from about 1.0 to about 40.0 parts by weight of HLCD in 1,000 to 10,000 parts by weight of NMP in a vehicle comprising between about 1,000 to about 5,000 part by weight of an acceptable alcohol, about 1,000 to about 10,000 parts by weight of polyethylene glycol, and about 1,000 to about 10,000 parts of a non-ionic surfactant. Suitable alcohols include dehydrated ethyl alcohol or benzyl alcohol, or combination of ethyl alcohol and benzyl alcohol. Suitable polyethylene glycols, include polyethylene glycol 300, polyethylene glycol 400, and polypropylene glycol. Suitable non-ionic surfactants include polysorbate-80 (Tween-80). In a preferred embodiment, the formulation of HLCD is supplied as an intravenous injectable in a vial comprising a solution of drug in a vehicle comprising ethyl alcohol and/or benzyl alcohol, citric acid, polyethylene glycol 400, and polysorbate (Tween 80).

Example 2

HIGHLY LIPOPHILIC CAMPTOTHECIN DERIVATIVE-NMP FORMULATION #2

A second formulation contains from about 1.0 to about 40.0 parts by weight of HLCD in 1,000 to 10,000 part of NMP further comprising between about 1,000 to 5,000 parts of an alcohol, about 100 to 5,000 parts by weight of an pharmaceutically acceptable acid and about 1,000 to 10,000 parts of polyethylene glycol 400. Suitable alcohols include ethyl alcohol, and benzyl alcohol. Suitable acids for this formulation include citric acid, hydrochloric acid or phosphoric acid. In a preferred embodiment 1 to about 20 parts of HLCD by weight is formulated in 1,000 to 10,000 parts of NMP, 1,000 to 10,000 parts of PEG-400, 1,000 to 5,000 parts by weight ethyl alcohol, and 1,000 to 5,000 parts of citric acid by weight.

Example 3

HIGHLY LIPOPHILIC CAMPTOTHECIN DERIVATIVE-NMP ORAL FORMULATION

An oral formulation of HLCD in soft gelatin capsules (comprised of gelatin/glycerin/sorbitol/purifiers) containing from about 1.0 part to about 40.0 parts by weight of HLCD dissolved in 1,000 to 10,000 parts of NMP, citric acid 1,000 to about 5,000 parts by weight, glycerin 0.5 to 2.5 parts by weight, and polyethylene glycol (PEG-300 or PEG-400) 1,000 to 10,000 parts by weight, ethyl alcohol 1,000 to 5,000 parts by weight, and taurocholic acid 1 to 10 parts by weight. The soft gelatin capsules may also be composed of any of a number of compounds used for this purpose including for example, a mixture of gelatin, glycerin, sorbitol, and parabens.

Example 4

7-ETHYL CAMPTOTHECIN-NMP FORMULATION

A formulation containing from about 1.0 to about 40.0 parts by weight of 7-ethyl camptothecin in 1,000 to 10,000 part of NMP further comprising between about 1,000 to 5,000 parts of an alcohol, about 100 to 5,000 parts by weight of an pharmaceutically acceptable acid and about 1,000 to 10,000 parts of polyethylene glycol 400. Suitable alcohols include ethyl alcohol, and benzyl alcohol. Suitable acids for this formulation include citric acid, hydrochloric acid or phosphoric acid. In a preferred embodiment 1 to about 20 parts of 7-ethyl camptothecin by weight is formulated in 1,000 to 10,000 parts of NMP, 1,000 to 10,000 parts of PEG-400, 1,000 to 5,000 parts by weight ethyl alcohol, and 1,000 to 5,000 parts of citric acid by weight.

Example 5

7-ETHYL-10-HYDROXY CAMPTOTHECIN-NMP FORMULATION

A formulation containing from about 1.0 to about 40.0 parts by weight of 7-ethyl-10-hydroxy camptothecin in 1,000 to 10,000 part of NMP further comprising between about 1,000 to 5,000 parts of an alcohol, about 100 to 5,000 parts by weight of an pharmaceutically acceptable acid and about 1,000 to 10,000 parts of polyethylene glycol 400.

Suitable alcohols include ethyl alcohol, and benzyl alcohol. Suitable acids for this formulation include citric acid, hydrochloric acid or phosphoric acid. In a preferred embodiment 1 to about 20 parts of 7-ethyl-10-hydroxy camptothecin by weight is formulated in 1,000 to 10,000 parts of NMP, 1,000 to 10,000 parts of PEG-400, 1,000 to 5,000 parts by weight ethyl alcohol, and 1,000 to 5,000 parts of citric acid by weight.

Example 6

10,11-METHYLENEDIOXY CAMPTOTHECIN-NMP FORMULATION

A formulation containing from about 1.0 to about 40.0 parts by weight of 10,11-methylenedioxy camptothecin in 1,000 to 10,000 part of NMP further comprising between about 1,000 to 5,000 parts of an alcohol, about 100 to 5,000 parts by weight of an pharmaceutically acceptable acid and about 1,000 to 10,000 parts of polyethylene glycol 400. Suitable alcohols include ethyl alcohol, and benzyl alcohol. Suitable acids for this formulation include citric acid, hydrochloric acid or phosphoric acid. In a preferred embodiment 1 to about 20 parts of 10,11-methylenedioxy by weight is formulated in 1,000 to 10,000 parts of NMP, 1,000 to 10,000 parts of PEG-400, 1,000 to 5,000 parts by weight ethyl alcohol, and 1,000 to 5,000 parts of citric acid by weight.

Example 7

10-BROMO CAMPTOTHECIN-NMP FORMULATION

A formulation containing from about 1.0 to about 40.0 parts by weight of 10-bromo camptothecin in 1,000 to 10,000 part of NMP further comprising between about 1,000 to 5,000 parts of an alcohol, about 100 to 5,000 parts by weight of an pharmaceutically acceptable acid and about 1,000 to 10,000 parts of polyethylene glycol 400. Suitable alcohols include ethyl alcohol, and benzyl alcohol. Suitable acids for this formulation include citric acid, hydrochloric acid or phosphoric acid. In a preferred embodiment 1 to about 20 parts of 10-bromo camptothecin by weight is formulated in 1,000 to 10,000 parts of NMP, 1,000 to 10,000 parts of PEG-400, 1,000 to 5,000 parts by weight ethyl alcohol, and 1,000 to 5,000 parts of citric acid by weight.

Example 8

Use of N-methyl-2-pyrrolidinone (NMP) in the Formulations

One of the key discoveries in the present invention is the unexpectedly high solubility of HLCD in N-methyl-2-pyrrolidinone (NMP). N-Methyl-2-pyrrolidinone is an organic liquid excipient and is also known as 1-methylpyrrolidinone, N-methyl-2-pyrrolidinone, 1-methyl-5-pyrrolidinone, methylpyrrolidinone, N-methyl pyrrolidinone, methylpyrrolidinone, N-methylpyrrolidone, N-methyl-2-pyrrolidone, M-pyrol, and NMP.

NMP exhibits a high degree of physiologic safety in mammals with the following LD50 values: (rat) oral—7000 mg/kg, intraperitoneal—2472 mg/kg, intravenous—2266 mg/kg, (mice) oral—7725 mg/kg, intraperitoneal—4429 mg/kg, intravenous—3605 mg/kg, (rabbit) skin—8000 mg/kg (Registry of Toxic Effects of Chemical Substances, 1983–84 Supplement, page 1628). NMP has been used to formulate etoposide (Etoposide, U.S. Pat. No. 4,772,589) and acridine derivatives (M-AMSA, U.S. Pat. No. 5,034, 397). Etoposide and acridine derivatives (1) are anticancer drugs; (2) are chemically unrelated to HLCD; (3) are more water soluble than HLCD; and (4) exert their antitumor effects by vastly different mechanisms than HLCD.

NMP has also been used for oral formulations of the antibiotic clarithromycin (Clarithromycin, WO patent #9,014,094) and other drugs. NMP is a key excipient of the instant invention which allows an exceptionally high degree of drug solubility of HLCD (range 1 mg/ml to 40 mg/ml) in NMP as a solution or suspension. An HLCD solution comprising NMP with or without other combinations of excipients described herein, which can be diluted with a parenteral vehicle such as sterile injectable water USP, 5% Dextrose solution for injection USP or 0.9% sodium chloride solution for injection USP, such that the amount of HLCD dissolved in the diluted infusion is from about 0.001 mg/ml to about 1.0 mg/ml, is taught in the present invention. The inventors have discovered that HLCD show remarkably high solubility in NMP compared to other common pharmaceutical solvents such as water, ethanol, benzyl alcohol, propylene glycol, PEG 300, PEG 400, dimethylisosorbide or dimethylacetamide (Table 5). This high solubility of HLCD in NMP makes NMP a unique and highly useful pharmaceutical solvent for making useful solutions or suspensions of HLCD.

| Solubility of Camptothecin in Various Solvents | |
|---|---|
| Solvent | Concentration, mg/ml |
| Milli-Q Water | 0.0002 |
| Ethanol | 0.051 |
| Benzyl alcohol | 1.674 |
| Propylene glycol | 0.281 |
| PEG 300 | 0.706 |
| Dimethylisosorbide | 0.928 |
| Dimethylacetamide | 5.000 |
| N-Methyl-2-pyrrolidinone (NMP) | >15.000 (range 15–20) |

NMP is inert with respect to undesirable chemical reactions with HLCD and is therefore a highly useful excipient to create solutions of HLCD in the lactone form. Further utility of NMP in the present invention is the discovery that NMP allows the introduction of additional excipients which further improve the overall utility of the HLCD dissolved in the NMP solution in a manner which are of additional benefit for parenteral or oral administration to human patients with cancer. The HLCD solution or suspension is prepared by mixing the desired components with NMP and adding a pharmaceutically acceptable acid to adjust the pH to 3–5.

REFERENCES

The following references may facilitate understanding or practice of certain aspects of the present invention. Inclusion of a reference in this list is not intended to and does not constitute an admission that the reference represents prior art with respect to the present invention.

| U.S. Pat. No. | | |
|---|---|---|
| 4,545,880 | 10/85 | Miyasaka et al. |
| 4,473,692 | 9/84 | Miyasaka et al. |
| 4,778,891 | 10/88 | Tagawa et al. |
| 5,061,800 | 10/91 | Miyasaka et al. |

-continued

| | | |
|---|---|---|
| 4,772,589 | 9/88 | Kaplan et al. |
| 5,034,397 | 7/91 | Kaplan et al. |
| World Patent | | |
| 9,014,094 | 11/90 | Hui et al. |

Other Publications

Barilero et al., Simultaneous Determination of the Camptothecin Analogue CPT-11 and Its Active Metabolite SN38 by High Performance Liquid Chromatography: Application to Plasma Pharmacokinetic Studies in Cancer Patients. J. Chromat. 575:275–280; 1992.

Bates et al., Solubilizing Properties of Bile Salt Solutions. I. Effect of Temperature and Bile Salt Concentration On Solubilization of Glutethimide, Griseofulvin and Hexostrol. Journal of Pharmaceutical Sciences, 55:191–199, (1966).

Bates et al., Rates of Dissolution of Griseofulvin and Hexestrol in Bile Salt Solutions. Chem. Abstracts 65:8680b, 1966.

Bates et al., Solubilizing Properties of Bile Salt Solutions on Glutethimide, Griseofulvin, and Hexestrol. Chem. Abstracts 64 :9517e 1966; 65:15165a, 1966.

Clavel, M. et al., Phase I Study of the Camptothecin Analogue CPT-11, Administered Daily for 3 Consecutive Days. Proc. Amer. Assoc. Cancer Res. 3:83, 1992.

Creaven, P. J. et al., Plasma Camptothecin (NSC-100880) Levels During a 5-Day Course of Treatment: Relation to Dose and Toxicity. Cancer Chem. Rep. 56: 573–578, 1972.

Culine, S., Phase I Study of the Camptothecin Analog CPT-11, Using a Weekly Schedule. Proc. of Amer. Soc. Clin. Onc. 11:110, 1992.

Emerson, D. L., In Vivo Antitumor Activity of Two New Seven-substituted Water-soluble Camptothecin Analogues. Cancer Research. 55: 603–609, 1995.

Fukuoka, M. et al., A Phase II Study of CPT-11, A New Derivative of Camptothecin, for Previously Untreated Small-Cell Lung Cancer. J. Clin. Onc. 10(1):16–20, 1992.

Giovanella BC, et al., DNA Topoisomerase I-Targeted Chemotherapy of Human Colon Cancer in Xenografts. Science 246: 1046–1048; 1989.

Gottlieb, J. A. et al., Preliminary Pharmacologic and Clinical Evaluation of Camptothecin Sodium (Nsc-100880). Cancer Chem. Rep. 54: 461–470, 1970.

Gottlieb, J. A. et al., Treatment of Malignant Melanoma With Camptothecin (NSC-100880). Cancer Chem. Rep. 56: 103–105, 1972.

Hsiang et al., Arrest of Replication Forks by Drug-stabilized Topoisomerase I-DNA Cleavable Complexes as a Mechanism of Cell Killing by Camptothecin Analogues. Cancer Res. 49:5077–5082, 1989.

Houghton, P. J. et al., Therapeutic Efficacy of the Topoisomerase I Inhibitor 7-Ethyl-10-(4-[1-piperidino]-1-piperidino)-carbonyloxy-camptothecin against Human Tumor Xenografts: Lack of Cross-Resistance in Vivo in Tumors with Acquired Resistance to the Topoisomerase I Inhibitor 9-Dimethylaminomethyl-10-hydroxycamptothecin. Cancer Res. 53:2823–2829, 1993.

Jaxel, C. et al., Structure Activity Study of the Actions of Camptothecin Derivatives on Mammalian Topoisomerase I: Evidence for a Specific Receptor Site and a relation to Antitumor Activity. Cancer Res. 49:1465–1469, 1989.

Kaneda, N. et al., Metabolism and Pharmacokinetics of the Camptothecin Analogue CPT-11 in the Mouse. Cancer Research 50:1715–1720, 1990.

Kano Y, et al., Effects of CPT-11 in Combination with other Anti-Cancer Agents in Culture. Int. J. Cancer 50:604–610;1992.

Kanzawa F, et al., Role of Carboxylesterase on Metabolism of Camptothecin Analog (CPT-11) in Non-Small Cell Lung Cancer Cell Line PC-7 Cells (Meeting Abstract). Proc. Annual Meet. Am. Assoc. Cancer Res. 33:A2552; 1992.

Kawato, Y. et al., Intracellular Roles of SN38, a Metabolite of the Camptothecin Derivative CPT-11, in the Antitumor Effect of CPT-11. Cancer Res. 51:4187–4191, 1991.

Kunimoto, T. et al., Antitumor Activity of 7-Ethyl-10-[4-(1-piperidino)-1-piperidino] Carbonyloxy-Camptothecin, a Novel Water Soluble Derivative of Camptothecin Against Murine Tumors. Cancer Res. 47:5944–5947, 1987.

Luzzio, M. J., et al., Synthesis and Antitumor Activity of Novel Water Soluble Derivatives of Camptothecin as Specific Inhibitors of Topoisomerase I. J. Med. Chem. 38: 395–401, 1995.

Malone et al., Desoxycholic Acid Enhancement of Orally Administered Reserpine. Journal of Pharmaceutical Sciences, 55:972–974 (1966).

Masuda, N. et al., CPT-11: A New Derivative of Camptothecin for the Treatment of Refractory or Relapsed Small-Cell Lung Cancer. J. Clin. Onc. 10(8):1225–1229 1992.

Moertel, C. G. et al., Phase II Study of Camptothecin (NSC-100880) in the Treatment of Advanced Gastrointestinal Cancer. Cancer Chem. Rep. 56: 95–101, 1972.

Muggia, F. M. et al., Phase I Clinical Trial of Weekly and Daily Treatment with Camptothecin (NSC-100880): Correlation with Preclinical Studies. Cancer Chem. Rep. 56: 515–521, 1972.

Negoro, S. et al., Phase I Study of Weekly Intravenous Infusions of CPT-11, a New Derivative of Camptothecin, in the Treatment of Advanced Non-Small Cell Lung Cancer. JNCI 83(16): 1164–1168, 1991.

Negoro, S. et al., Phase II Study of CPT-11, New Camptothecin Derivative, in Small Cell Lung Cancer. Proc. of Amer. Soc. Clin. Onc. 10:241, 1991.

Niimi S, et al., Mechanism of Cross-Resistance to a Camptothecin Analogue (CPT-11) in a Human Ovarian Cancer Cell Line Selected by Cisplatin. Cancer Res. 52:328–333; 1992.

Ohe, Y. et al., Phase I Study and Pharmacokinetics of CPT-11 with 5-Day Continuous Infusion. JNCI 84(12):972–974, 1992.

Ohno, R. et al., An Early Phase II Study of CPT-11: A New Derivative of Camptothecin, for the Treatment of Leukemia and Lymphoma. J. Clin. Onc. 8(11):1907–1912, 1990.

Pantazis, P. et al., Cytotoxic Efficacy of 9-Nitrocamptothecin in the Treatment of Human Malignant Melanoma Cells in Vitro. Cancer Research. 54: 771–776, 1994.

Pommier, Y. et al., Camptothecins: Mechanism of Action and Resistance (Meeting Abstract). Cancer Investigation, Presented at the "Chemotherapy Foundation Symposium X Innovative Cancer Chemotherapy for Tomorrow," page 3, 1992.

Potmesil, M. et al., Preclinical and Clinical Development of DNA Topoisomerase I Inhibitors in the United States. in Andoh,T., Ikeda, H. Oguro, M. (eds): Molecular Biology of DNA Topoisomerases and Its Application to Chemotherapy. Boca Raton, Fla., CRC Press, Inc. 301–311, 1993.

Rivory, L. P., et al., Kinetics of the in Vivo Interconversion of the Carboxylate and Lactone Forms of Irinotecan (CPT-11) and of Its Metabolite SN-38 in Patients. Cancer Research. 54:6330–6333, 1994.

Rothenberg, M. L. et al., A Phase I and Pharmacokinetic Trial of CPT-11 in Patients with Refractory Solid Tumors. Amer. Soc. Clin. Onc. 11:113, 1992.

Rothenberg, M. L., Kuhn, J. G., Burris, H. A., Nelson, J., Eckardt, J. R., Tristan-Morales, M., Hilsenbeck, S. G., Weiss, G. R., Smith, L. S., Rodriguez, G. I., Rock, M. K., Von Hoff, D. D. Phase I and Pharmacokinetic Trial of Weekly CPT-11. Journal of Clinical Oncology. 11:2194–2204 (1993).

Rowinsky, E. et al., Phase I Pharmacologic Study of CPT-11, A Semisynthetic Topoisomerase I-Targeting Agent, on a Single-Dose Schedule (Meeting Abstract). Proc. of Amer. Soc. Clin. Onc. 11:115, 1992.

Sawada S. et al., Synthesis and Antitumor Activity of 20 (S)-Camptothecin Derivatives: Carbonate-Linked, Water Soluble, Derivatives of 7-Ethyl-10-hydroxycamptothecin. Chem. Pharm. Bull. 39:14446–1454; 1991.

Shimada, Y. et al., Phase II Study of CPT-11, New Camptothecin Derivative, In the Patients with Metastatic Colorectal Cancer. Proc. of Amer. Soc. Clin. Onc. 10:135, 1991.

Supko, J. G. et al., Pharmacokinetics of the 9-Amino and 10,11-Methylenedioxy Derivatives of Camptothecin in Mice. Cancer Res. 53: 3062–3069, 1993.

Takeuchi, S. et al., Late Phase II Study of CPT-11, A Topoisomerase I Inhibitor, In Advanced Cervical Carcinoma (CC) (Meeting Abstract). Proc. of Amer. Soc. Clin. Onc. 11:224, 1992.

Wall, M. E. et al., Camptothecin and Taxol: Discovery to Clinic-Thirteenth Bruce F. Cain Memorial Award Lecture. Cancer Research. 55:753–760, 1995.

Wall, M. E. et al., Camptothecin, in Cassady JM, Douros JD (eds): Anticancer Agents Based on Natural Product Models, San Diego, Calif., Academic Press, 1980, 417–436.

Wall, M. E. et al., Plant Antitumor Agents: Synthesis and Structure Activity of Novel Camptothecin Anaglogs. J. Med. Chem., 36:2689–2700 (1993).

Westergaard et al., The Mechanism Whereby Bile Acid Micelles Increase the Rate of Fatty Acid and Cholesterol Uptake Into the Intestinal Mucosal Cell. Journal of Clinical Investigation, 58: 97–108 (1976)).

The foregoing description has been directed to particular embodiments of the invention in accordance with requirements of the Patent Statutes for the purposes of illustration and explanation. It will be apparent, however, to those skilled in this art, that many modifications, changes and variations in the claimed antitumor compositions, solutions, methods of administration of the antitumor compositions set forth will be possible without departing from the scope and spirit of the claimed invention. It is intended that the following claims be interpreted to embrace all such modifications and changes.

What is claimed is:

1. A solution or suspension comprising a substituted camptothecin having a water solubility of 5 micrograms or less than 5 micrograms per milliliter wherein said camptothecin has substitutions on the A-ring and on the B-ring and wherein said substituted camptothecin is dissolved or suspended in an effective amount of N-methyl-2-pyrrolidinone.

2. The solution or suspension of claim 1 further comprises a pharmaceutically acceptable acid.

3. The solution or suspension of claim 2 wherein said acid is a carboxylic acid.

4. The solution or suspension of claim 2 wherein said acid is selected from the group consisting of acetic acid, citric acid, fumaric acid, maleic acid, ascorbic acid, gluconic acid, and lactic acid.

5. The solution or suspension of claim 2 wherein said acid is a mineral acid.

6. The solution or suspension of claim 5 wherein said acid is selected from a group consisting of hydrochloric acid and phosphoric acid.

7. The solution of suspension of claim 2 wherein said acid is selected from the group consisting of acetic acid, citric acid, fumaric acid, maleic acid, ascorbic acid, phosphoric acid, gluconic acid, lactic acid, and hydrochloric acid.

8. The solution or suspension of claim 2 further comprising a lower alcohol.

9. The solution or suspension of claim 8 wherein said lower alcohol is selected from the group consisting of ethanol and benzyl alcohol.

10. The solution or suspension of claim 2 further comprising a polyethylene glycol.

11. The solution or suspension of claim 10 wherein said polyethylene glycol is selected from a group consisting of PEG-300 and PEG-400.

12. The solution or suspension of claim 2 further comprising a non-ionic surfactant.

13. The solution or suspension of claim 12 wherein said non-ionic surfactant is polysorbate-80 (Tween-80).

14. The solution or suspension of claim 2 further comprising a polyethylene glycol and a non-ionic surfactant.

15. The solution or suspension of claim 2 further comprising a lower alcohol, polyethylene glycol and a non-ionic surfactant.

16. The solution or suspension of claim 2 further comprising 1 to 10 parts by weight of taurocholic acid or a pharmaceutically acceptable salt thereof.

17. The solution or suspension of claim 2 further comprising 1 to 10 parts by weight of taurocholic acid or a pharmaceutically acceptable salt thereof.

18. The solution or suspension of claim 8 further comprising 1 to 10 parts by weight of taurocholic acid or a pharmaceutically acceptable salt thereof.

19. The solution or suspension of claim 10 further comprising 1 to 10 parts by weight of taurocholic acid or a pharmaceutically acceptable salt thereof.

20. The solution or suspension of claim 12 further comprising 1 to 10 parts by weight of taurocholic acid or a pharmaceutically acceptable salt thereof.

21. The solution or suspension of claim 14 further comprising 1 to 10 parts by weight of taurocholic acid or a pharmaceutically acceptable salt thereof.

22. The solution or suspension of claim 15 further comprising 1 to 10 parts by weight of taurocholic acid or a pharmaceutically acceptable salt thereof.

23. The solution or suspension of claim 1 wherein said solution or suspension comprises from about 1.0 mg to about 40.0 mg activity per ml of solution or suspension of an A-ring substituted camptothecin having a water solubility of less than 5 micrograms per ml of water.

24. The solution or suspension of claims 1, 2, 8, 10, 12, 14, or 15 wherein said solution or suspension is prepared and sterilized for oral, intrapleural, intrathecal, intracisternal, intravesicular, intraperitoneal, topical or intravenous administration.

25. The solution or suspension of claims 1, 2, 8, 10, 12, 14, or 15 wherein said solution or suspension is encapsulated within a hard gelatin capsule or a soft gelatin capsule.

* * * * *